US012658284B2

(12) United States Patent
Oboukhov et al.

(10) Patent No.: US 12,658,284 B2
(45) Date of Patent: Jun. 16, 2026

(54) REFERENCE MARKS STORING EMBEDDED OLIGO INDEX IN DNA DATA STORAGE

(71) Applicant: Western Digital Technologies, Inc., San Jose, CA (US)

(72) Inventors: Iouri Oboukhov, Rochester, MN (US); Niranjay Ravindran, Rochester, MN (US); Richard Galbraith, Rochester, MN (US); Austin Striegel, Rochester, MN (US)

(73) Assignee: Western Digital Technologies, Inc., San Jose, CA (US)

( * ) Notice: Subject to any disclaimer, the term of this patent is extended or adjusted under 35 U.S.C. 154(b) by 81 days.

(21) Appl. No.: 18/750,586

(22) Filed: Jun. 21, 2024

(65) Prior Publication Data

US 2025/0391513 A1 Dec. 25, 2025

(51) Int. Cl.
 *G16B 50/50* (2019.01)
 *G16B 30/00* (2019.01)
 (Continued)

(52) U.S. Cl.
 CPC ............. *G16B 50/50* (2019.02); *G16B 30/00* (2019.02); *G11C 13/02* (2013.01); *G16B 50/40* (2019.02);
 (Continued)

(58) Field of Classification Search
 CPC ........ G16B 50/50; G16B 30/00; G16B 50/30; G16B 50/40; H03M 13/1105; H03M 13/1148; H03M 13/37
 See application file for complete search history.

(56) References Cited

U.S. PATENT DOCUMENTS 8,407,554 B2 3/2013 Kermani
8,937,564 B2 1/2015 Aloni
 (Continued)

FOREIGN PATENT DOCUMENTS

CN 118138060 A 6/2024
EP 3416076 A1 12/2018
 (Continued)

OTHER PUBLICATIONS

Zhang et al., "Soft-Decision Decoding for DNA-Based Data Storage," 2018 International Symposium on Information Theory and Its Applications (ISITA), Singapore, 2018, pp. 16-20, (Year: 2018).
 (Continued)

*Primary Examiner* — Joseph J Lauture
(74) *Attorney, Agent, or Firm* — Patent Law Works LLP

(57) ABSTRACT

Example systems and methods for embedding an oligo index in a series of reference marks along the oligo for DNA data storage are described. A data unit may be encoded in oligos that include reference marks at predetermined intervals along the length of each oligo that encode the oligo index, generally in multiple copies encoded with varying symmetries. During decoding, the reference marks may be analyzed through multiple correlation matrices to determine a most likely set of values for the oligo index. In some configurations, the same reference marks may be processed through another correlation matrix to determine and correct insertions and deletions based on multiple copies of the oligo, as identified by the decoded oligo indices in those copies.

20 Claims, 11 Drawing Sheets

600

Determine Data Unit
610

Determine User Data for Oligo
612

Determine Oligo Index
614

Modulate User Data
616

Determine Redundancy Data
618

Determine Reference Mark Intervals/Frequency 620

Determine Number of Copies of Oligo Index 622

Map Oligo Index to Sets of Reference Marks 624

Determine Translations for Different Index Copies 626

Order Translations Across Reference Marks 628

Insert Reference Marks 630

Output Write Data for Oligo Synthesis 632

(51) Int. Cl.
    *G11C 13/02*       (2006.01)
    *G16B 50/40*      (2019.01)
    *H03M 13/11*     (2006.01)

(52) U.S. Cl.
    CPC ..... *H03M 13/1105* (2013.01); *H03M 13/1148*
                                         (2013.01)

(56)            References Cited

U.S. PATENT DOCUMENTS

| | | | |
|---|---|---|---|
| 9,234,239 | B2 | 1/2016 | Sikora |
| 9,830,553 | B2 | 11/2017 | Chen |
| 10,027,347 | B2 | 7/2018 | Le Scouarnec |
| 10,370,246 | B1 | 8/2019 | Milenkovic |
| 10,423,341 | B1 | 9/2019 | Kermani |
| 10,566,077 | B1 | 2/2020 | Milenkovic |
| 10,650,312 | B2 | 5/2020 | Roquet |
| 10,742,233 | B2 | 8/2020 | Erlich |
| 10,810,495 | B2 | 10/2020 | Roth |
| 10,818,378 | B2 | 10/2020 | Hutchison, III |
| 10,917,109 | B1 | 2/2021 | Dimopoulou |
| 10,956,806 | B2 | 3/2021 | Masuda |
| 11,017,170 | B2 | 5/2021 | Yin |
| 11,093,547 | B2 | 8/2021 | Su |
| 11,098,303 | B2 | 8/2021 | Zhuang |
| 11,227,219 | B2 | 1/2022 | Roquet |
| 11,249,941 | B2 | 2/2022 | Unidad |
| 11,435,905 | B1 | 9/2022 | Kermani |
| 11,755,649 | B2 | 9/2023 | Wei |
| 11,755,922 | B2 | 9/2023 | Milenkovic |
| 11,763,169 | B2 | 9/2023 | Roquet |
| 2004/0191788 | A1 | 9/2004 | Gleba |
| 2007/0042372 | A1 | 2/2007 | Arita |
| 2010/0199155 | A1 | 8/2010 | Kermani |
| 2011/0172975 | A1 | 7/2011 | Silva Filho |
| 2011/0269119 | A1 | 11/2011 | Hutchison |
| 2017/0109229 | A1 | 4/2017 | Huetter |
| 2017/0134045 | A1 | 5/2017 | Huetter |
| 2018/0046921 | A1 | 2/2018 | Chen |
| 2019/0130280 | A1 | 5/2019 | Erden |
| 2019/0362814 | A1 | 11/2019 | Roquet |
| 2019/0363739 | A1 | 11/2019 | Erlich |
| 2020/0043568 | A1 | 2/2020 | Sikora |
| 2020/0185057 | A1 | 6/2020 | Leake |
| 2020/0193301 | A1 | 6/2020 | Roquet |
| 2020/0211677 | A1 | 7/2020 | Fan |
| 2021/0024924 | A1 | 1/2021 | Qi |
| 2021/0050073 | A1 | 2/2021 | Chen |
| 2021/0074380 | A1 | 3/2021 | Yekhanin |
| 2021/0079382 | A1 | 3/2021 | Leake |
| 2021/0098081 | A1 | 4/2021 | Yekhanin |
| 2021/0108194 | A1 | 4/2021 | Nathaniel |
| 2021/0166159 | A1 | 6/2021 | Rubenstein |
| 2021/0202032 | A1 | 7/2021 | Krsticevic |
| 2021/0210171 | A1 | 7/2021 | Stirparo |
| 2021/0225461 | A1 | 7/2021 | Merriman |
| 2022/0002781 | A1 | 1/2022 | Harness |
| 2022/0044763 | A1 | 2/2022 | Karimi |
| 2022/0364991 | A1 | 11/2022 | Wanunu |
| 2023/0027270 | A1 | 1/2023 | Rubenstein |
| 2023/0257801 | A1 | 8/2023 | Brodin |
| 2023/0317164 | A1 | 10/2023 | Roquet |
| 2024/0184666 | A1 | 6/2024 | Oboukhov |
| 2024/0185959 | A1* | 6/2024 | Oboukhov ............. G16B 50/50 |
| 2024/0257147 | A1 | 8/2024 | Owen |
| 2025/0020657 | A1 | 1/2025 | Graige |
| 2025/0037039 | A1 | 1/2025 | Rosenstein |
| 2025/0088203 | A1 | 3/2025 | Oboukhov |

FOREIGN PATENT DOCUMENTS

| | | | |
|---|---|---|---|
| WO | 2018148260 | A1 | 8/2018 |
| WO | 2019046768 | A1 | 3/2019 |
| WO | 2021072398 | A1 | 4/2021 |
| WO | 2021105974 | A1 | 6/2021 |
| WO | 2021231493 | A1 | 11/2021 |

OTHER PUBLICATIONS

Dimopoulou et al., "Storing Digital Data Into DNA: A Comparative Study Of Quaternary Code Construction," ICASSP 2020-2020 IEEE International Conference on Acoustics, Speech and Signal Processing , pp. 4332-4336, (2020).

Hamoum et al. "DNA Data Storage Algorithms and Synchronization", Information Theory [math.IT]. University Bretagne Sud, (2022).

Qin, et al. "Robust Multi-read Reconstruction from Contaminated Custers Using Deep Neural Network for DNA Storage." arXiv preprint arXiv:2210.11106. Oct. 31, 2022 (Oct. 31, 2022) whole document.

Zhang et al. Rbec: a Tool for Analysis of Amplicon Sequencing Data from Synthetic Microbial Communities. ISME communications, 1(1), 73. Jan. 17, 2021 (Jan. 17, 2021) whole document (2021).

Lu et al., "Design of Nonbinary Error Correction Codes With a Maximum Run-length Constraint to Correct a Single Insertion or Deletion Error for Dna Storage", Institute of Electrical and Electronics Engineers (IEEE), vol. 9, pp. 135354-135363, (2021).

Cai et al., "Correcting a Single Indel/Edit for DNA-Based Data Storage: Linear-Time Encoders and Order-Optimality", EEE Transactions on Information Theory, vol. 67, No. 6, pp. 3438-3451, (2021).

Chen et al., "Multiple Interleaved RS Codes for Data Storage Using Up to Mb-scale Synthetic DNA in Living Cells", Synthetic Biology Journal, vol. 2, Issue 3, pp. 428-443, (2021).

Goto et al., "Coding of Insertion-deletion-substitution Channels Without Markers", 2016 IEEE International Symposium on Information Theory, pp. 635-639, (2016).

Khuat et al., "A Quaternary Code Correcting a Burst of at Most Two Deletion or Insertion Errors in DNA Storage", Entropy, vol. 23, No. 12, pp. 1592, (2021).

Kiah et al., "Codes for DNA Sequence Profiles", IEEE Transactions on Information Theory, vol. 62, No. 6, pp. 3125-3146, (2016).

Limbachiya et al., "On Optimal Family of Codes for Archival DNA Storage", Seventh International Workshop on Signal Design and its Applications in Communications, pp. 123-127, (2015).

Nakata et al., "Synchronization and Asymmetric Error Correction for Nanopore Sequencing," 2021 IEEE International Conference on Consumer Electronics—Taiwan, pp. 1-2, (2021).

Yin et al., "Design of Constraint Coding Sets for Archive DNA Storage", IEEE/ACM Transactions on Computational Biology and Bioinformatics, vol. 19, No. 6, pp. 3384-3394, (2022).

Chauhan et al., "Portable and Error-Free DNA-Based Data Storage", 2021 4th International Conference on Recent Developments in Control, pp. 418-421, (2021).

Deng et al., "Optimized Code Design for Constrained DNA Data Storage With Asymmetric Errors", IEEE Access, vol. 7, pp. 84107-84121, (2019).

Jain et al., "Duplication-Correcting Codes for Data Storage in the DNA of Living Organisms", IEEE Transactions on Information Theory, vol. 63, No. 8, pp. 4996-5010 (2017).

Press et al., "HEDGES Error-correcting Code for DNA Storage Corrects Indels and Allow Sequence Constraints", Proc Natl Acad Sci USA, vol. 117, No. 31, pp. 18489-18496, (2020).

Wei et al., "Improved Coding Over Sets for DNA-Based Data Storage", IEEE Transactions on Information Theory, vol. 68, No. 1, pp. 118-129, (2022).

Wu et al., "HD-Code: End-to-End High Density Code for DNA Storage", IEEE Transactions on NanoBioscience, vol. 20, No. 4, pp. 455-463, (2021).

Yan et al., "New Levenshtein-Marker Code for DNA-based Data Storage Capable of Correcting Multiple Edit Errors", TechRxiv. (2021).

Hamoum et al., "Channel Model with Memory for DNA Data Storage with Nanopore Sequencing", 2021 11th International Symposium on Topics in Coding , pp. 1-5, (2021).

Christner et al., "DNA Data Storage—DNA Data Storage Alliance—Rosetta Stone Initiative", Storage Networking Industry Association, Storage Developer Conference, Fremont, CA, Sep. 12-15, 2022.

(56)　　　　　References Cited

OTHER PUBLICATIONS

Gervasio et al., "DNA Data Storage—A Decade of Coding and Decoding, How Far Have We Got?", Storage Networking Industry Association, Storage Developer Conference, Fremont, CA, Sep. 12-15, 2022.

Landsman et al., "DNA Data Storage Alliance: Building a DNA Data Storage Ecosystem", Storage Networking Industry Association, Storage Developer Conference, Fremont, CA, Sep. 12-15, 2022.

Marelli et al., "DNAssim: A Full System Simulator for DNA Storage", Storage Networking Industry Association, Storage Developer Conference, Fremont, CA, Sep. 12-15, 2022.

OG US et al., "The Looming Need for Molecular Storage", Storage Networking Industry Association, Storage Developer Conference, Fremont, CA, Sep. 12-15, 2022.

Piantanida et al., "Nucleic Acid Memory—Super Resolution Microscopy Enhances Novel Approach to DNA Data Storage", Boise State University, Storage Developer Conference, Fremont, CA, Sep. 12-15, 2022.

Reis et al., "Coding and Decoding, an Experience from a Brazilian Research Center", Storage Networking Industry Association, Storage Developer Conference, Fremont, CA, Sep. 12-15, 2022.

Dimopoulou et al., "Image storage onto synthetic DNA", Signal Processing: Image Communication, vol. 97, 116331, May 27, 2021, Sections 5.1-5.2; and figure B.3.

* cited by examiner

100

140

130

Figures 4A, 4B:
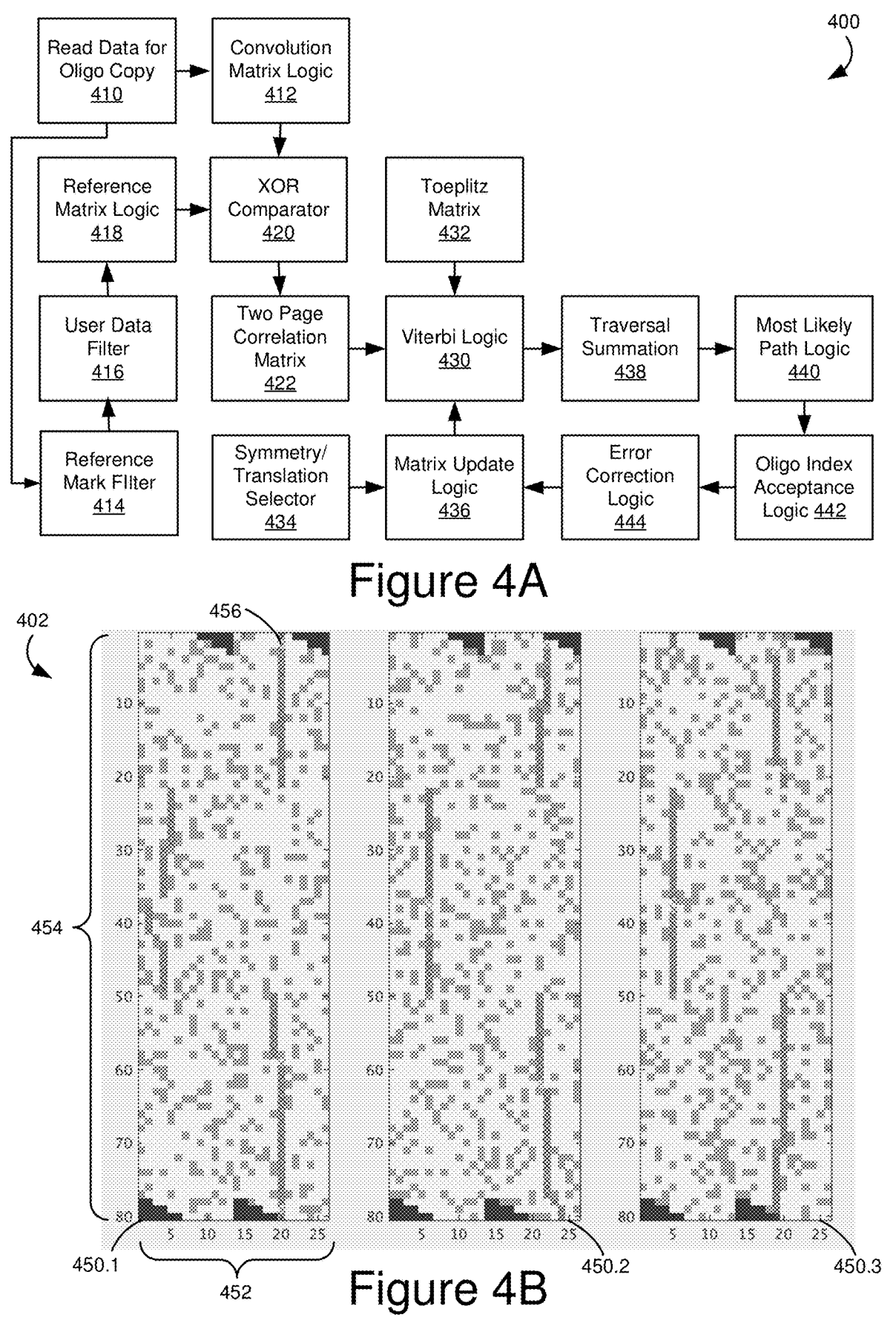

400

| Read Data for Oligo Copy 410 | → | Convolution Matrix Logic 412 |
|---|---|---|

| Reference Matrix Logic 418 | → | XOR Comparator 420 | | Toeplitz Matrix 432 |
|---|---|---|---|---|

| User Data Filter 416 | Two Page Correlation Matrix 422 | Viterbi Logic 430 | Traversal Summation 438 | Most Likely Path Logic 440 |
|---|---|---|---|---|

| Reference Mark Filter 414 | Symmetry/ Translation Selector 434 | Matrix Update Logic 436 | Error Correction Logic 444 | Oligo Index Acceptance Logic 442 |
|---|---|---|---|---|

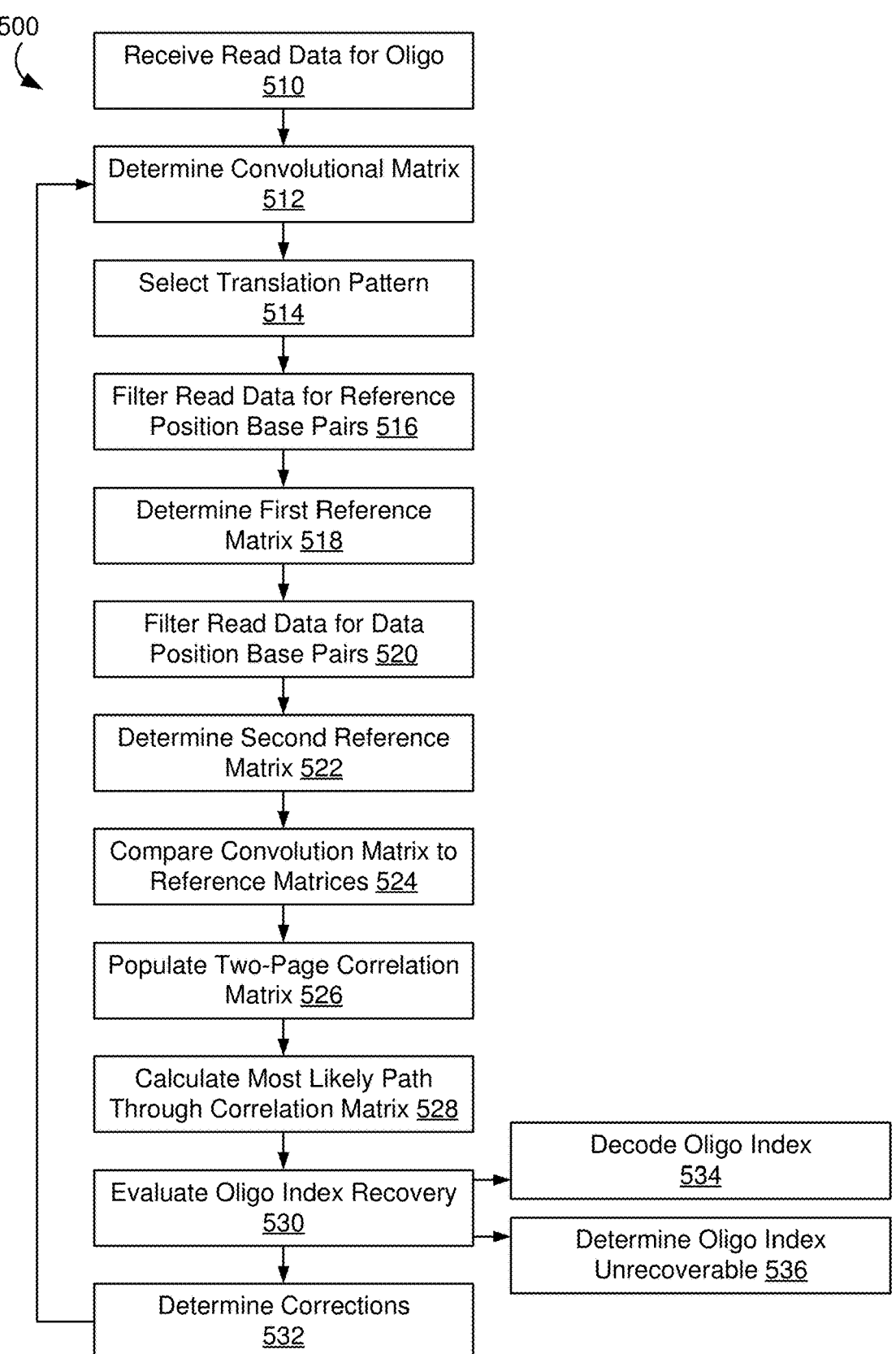

Receive Read Data for Oligo
510

Determine Convolutional Matrix
512

Select Translation Pattern
514

Filter Read Data for Reference
Position Base Pairs 516

Determine First Reference
Matrix 518

Filter Read Data for Data
Position Base Pairs 520

Determine Second Reference
Matrix 522

Compare Convolution Matrix to
Reference Matrices 524

Populate Two-Page Correlation
Matrix 526

Calculate Most Likely Path
Through Correlation Matrix 528

Evaluate Oligo Index Recovery
530

Decode Oligo Index
534

Determine Oligo Index
Unrecoverable 536

Determine Corrections
532

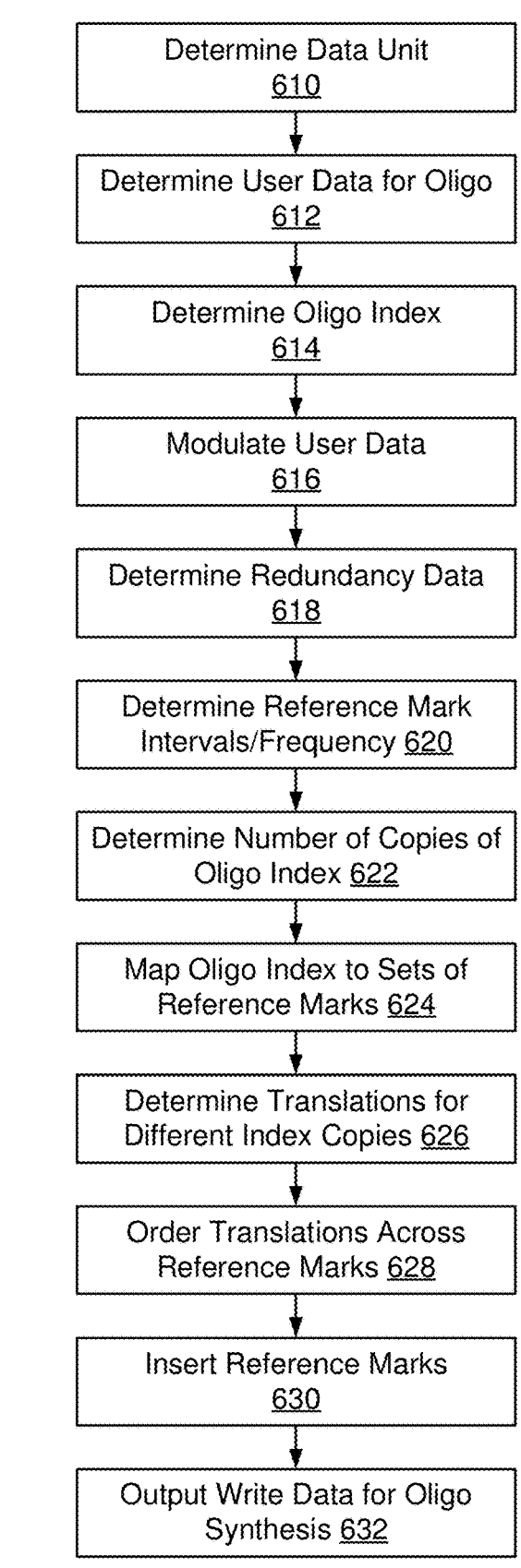

Determine Data Unit
610

Determine User Data for Oligo
612

Determine Oligo Index
614

Modulate User Data
616

Determine Redundancy Data
618

Determine Reference Mark
Intervals/Frequency 620

Determine Number of Copies of
Oligo Index 622

Map Oligo Index to Sets of
Reference Marks 624

Determine Translations for
Different Index Copies 626

Order Translations Across
Reference Marks 628

Insert Reference Marks
630

Output Write Data for Oligo
Synthesis 632

Figure 6

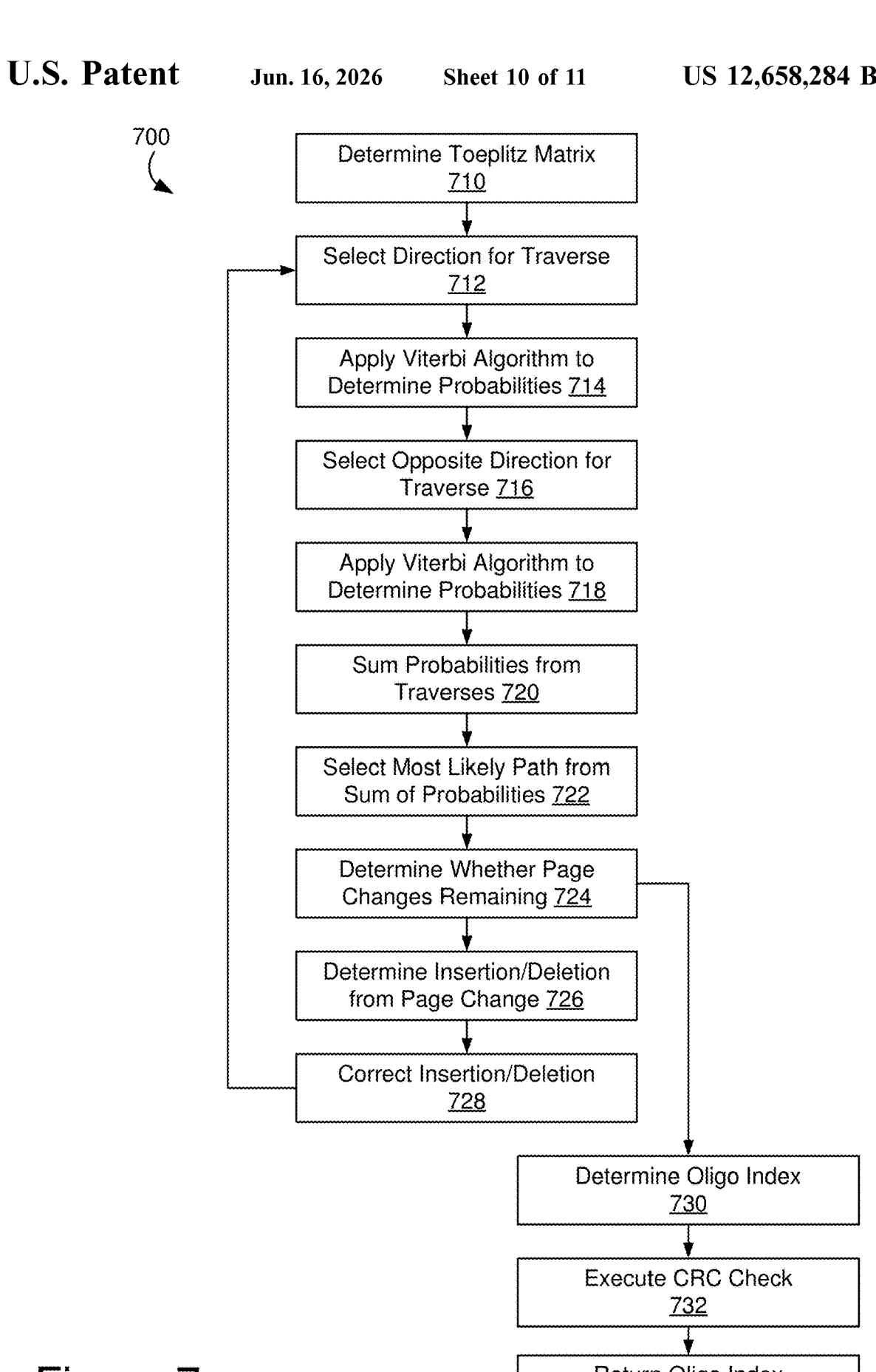

700

Determine Toeplitz Matrix
710

Select Direction for Traverse
712

Apply Viterbi Algorithm to
Determine Probabilities 714

Select Opposite Direction for
Traverse 716

Apply Viterbi Algorithm to
Determine Probabilities 718

Sum Probabilities from
Traverses 720

Select Most Likely Path from
Sum of Probabilities 722

Determine Whether Page
Changes Remaining 724

Determine Insertion/Deletion
from Page Change 726

Correct Insertion/Deletion
728

Determine Oligo Index
730

Execute CRC Check
732

Return Oligo Index
734

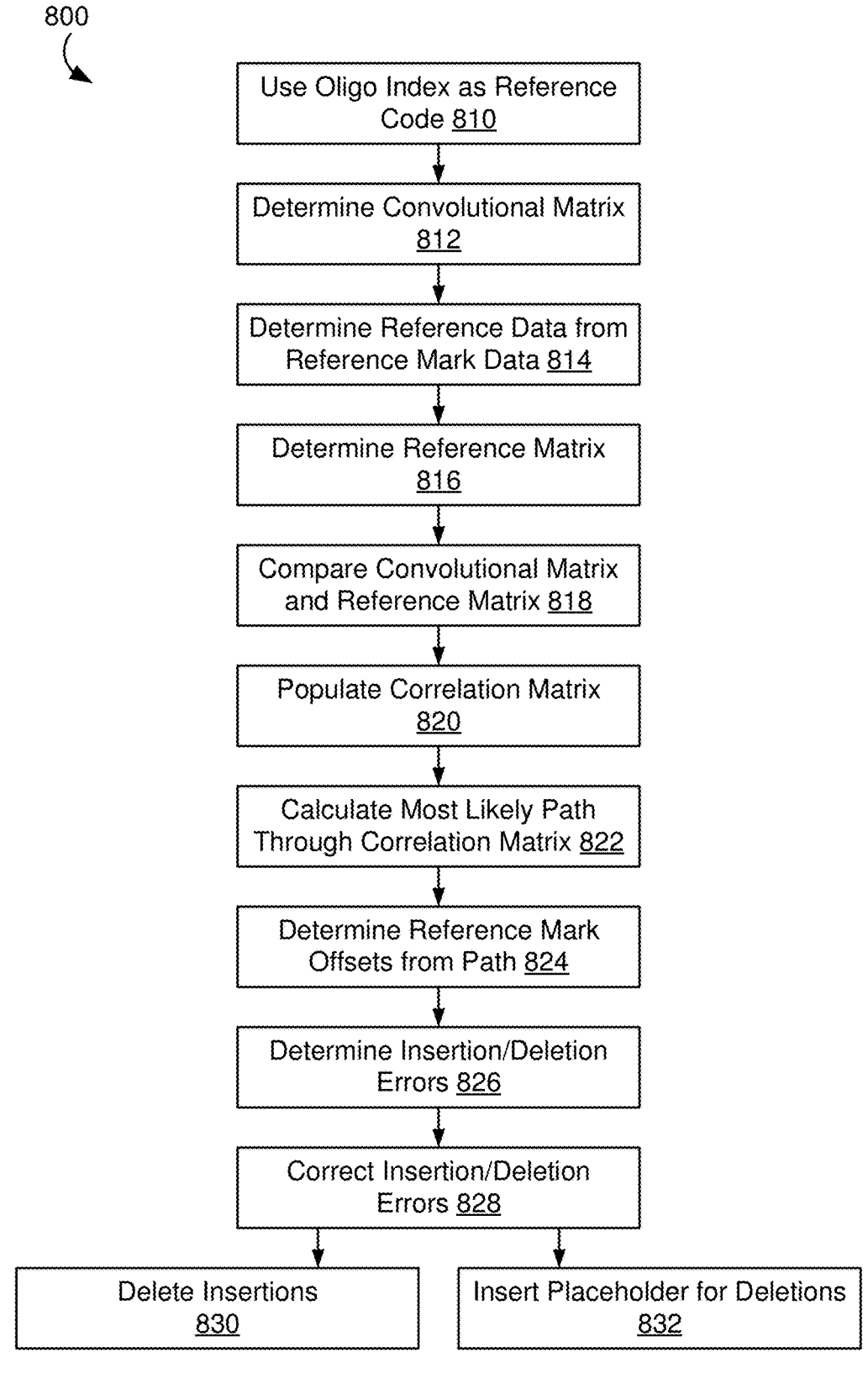

Use Oligo Index as Reference Code 810

Determine Convolutional Matrix 812

Determine Reference Data from Reference Mark Data 814

Determine Reference Matrix 816

Compare Convolutional Matrix and Reference Matrix 818

Populate Correlation Matrix 820

Calculate Most Likely Path Through Correlation Matrix 822

Determine Reference Mark Offsets from Path 824

Determine Insertion/Deletion Errors 826

Correct Insertion/Deletion Errors 828

Delete Insertions 830

Insert Placeholder for Deletions 832

Figure 8

REFERENCE MARKS STORING EMBEDDED OLIGO INDEX IN DNA DATA STORAGE

TECHNICAL FIELD

The present disclosure relates to deoxyribonucleic acid (DNA) data storage. In particular, the present disclosure relates to error correction for data stored as a set of synthetic DNA oligos.

BACKGROUND

DNA is a promising technology for information storage. It has potential for ultra-dense 3D storage with high storage capacity and longevity. Currently, technology of DNA synthesis provides tools for synthesis and manipulation of relatively short synthetic DNA chains (oligos). For example, some oligos may include 40 to 350 bases encoding twice that number of bits in configurations that use bit symbols mapped to the four DNA nucleotides or sequences thereof. Due to the relatively short payload capacity of oligos, Reed-Solomon error correction codes have been applied to individual oligos.

There is a need for technology that applies more efficient error correction codes to DNA data storage and retrieval.

BRIEF DESCRIPTION OF THE DRAWINGS

The techniques introduced herein are illustrated by way of example, and not by way of limitation, in the figures of the accompanying drawings in which like reference numerals are used to refer to similar elements.

FIG. 5 is an example method for recovering oligo index data stored in embedded reference marks in oligo read data, such as using the decoding systems of FIGS. 2 and 4A.

FIG. 6 is an example method for encoding reference marks in oligos, such as using the encoding system of FIG. 2.

FIG. 7 is an example method for determining probabilities of reference mark shifts using a Viterbi algorithm, such as using the decoding systems of FIGS. 2 and 4A.

FIG. 8 is an example method for correcting insertions and deletions for recovery of user data based on embedded reference marks, such as using the decoding system of FIG. 2.

SUMMARY

Figure 1A:
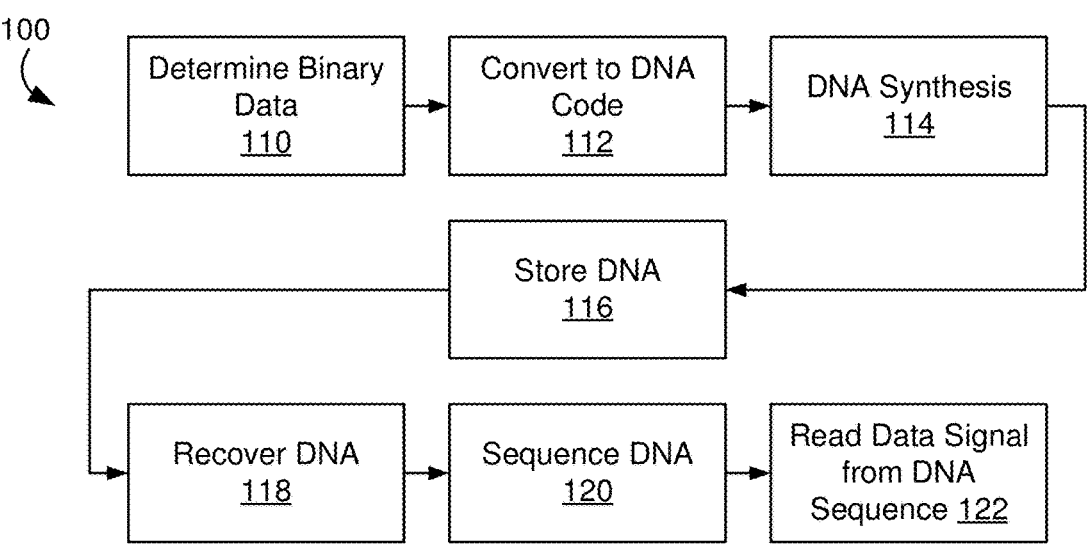
FIG. 1A is a block diagram of a prior art DNA data storage process.

Various aspects for using reference marks to store embedded oligo index data for encoding and decoding data stored in an oligo pool for DNA data storage are described.

One general aspect includes a system that includes an encoder configured to: determine an oligo for encoding a data unit, where the oligo encodes a number of symbols corresponding to user data in the data unit; insert a plurality of reference marks at a predetermined interval along a length of the oligo, where at least one set of reference marks in the plurality of reference marks encodes an oligo index and the predetermined interval equals a fixed data length between sequential reference marks; and output write data for the oligo for synthesis of the oligo.

Implementations may include one or more of the following features. The predetermined interval of the plurality of reference marks corresponds to a single base pair between sequential reference marks. The oligo index may include an oligo address and a cyclic redundancy check code. The plurality of reference marks may include a plurality of copies of the oligo index. Each copy of the oligo index may include a different set of reference marks of the at least one set of reference marks and at least two copies of the oligo index may include different translations of the oligo index that order the corresponding sets of reference marks in different translation orders. Each copy of the oligo index may occupy a predetermined set of positions in the plurality of reference marks and have a known translation order for that predetermined set of positions and corresponding set of reference marks. The different translation orders may be selected from mirror symmetry and translational symmetry using circular offset values less than a length of the oligo index. The plurality of reference marks may include a reference number of base pairs in the oligo; the reference number of base pairs may be a multiple of the length of the oligo index; the multiple may be at least equal to a number of the plurality of copies; and the number of the plurality of copies may be at least four. The different sets of reference marks of the at least two copies may be interleaved along the length of the oligo index. The system may include an index decoder configured to: receive read data determined from sequencing the oligo; determine, from the read data, a convolutional matrix for the oligo, where each column of the convolutional matrix corresponds to a base pair offset of the read data for the oligo; determine, from the read data, a first reference matrix based on a first sequence of reference positions at an encoded frequency of the plurality of reference marks; determine, from the read data, a second reference matrix based on a second sequence of reference positions at the encoded frequency of the plurality of reference marks; determine a first correlation matrix based on a comparison of the convolutional matrix to the first reference matrix; determine a second correlation matrix based on a comparison of the convolutional matrix and the second reference matrix; determine a most likely path through a combination of the first correlation matrix and the second correlation matrix based on a series of probabilities of moving between corresponding rows in the first correlation matrix and the second correlation matrix and loop decoding for different symmetries of the plurality of copies of the oligo index; and decode the oligo index based on the most likely path and the plurality of copies of the oligo index.

Another general aspect includes a system that includes a reference mark decoder configured to receive, based on oligos with a same decoded oligo index, read data determined from sequencing at least two copies of an oligo where the oligo encodes a number of symbols corresponding to user data in a data unit and a plurality of reference marks at a predetermined interval along a length of the oligo. At least one set of reference marks in the plurality of reference marks encodes an oligo index and the predetermined interval equals a fixed data length between sequential reference marks. The reference mark decoder is further configured to: populate a reference mark correlation matrix based on a comparison of reference mark positions in a first copy of the oligo to reference mark positions in a second copy of the oligo; determine a most likely path through the reference mark correlation matrix corresponding to offset values for the plurality of reference marks; determine, based on at least one offset value for the plurality of reference marks, an insertion or deletion in a data segment between sequential reference marks; and correct symbol alignment in the data segment to compensate for the insertion or deletion.

Implementations may include one or more of the following features. The system may include a user data decoder configured to: decode the user data from the read data using an error correction code and corresponding redundancy data; and output, based on the decoded user data, the data unit.

Stille another general aspect includes a method that includes: determining an oligo for encoding a data unit, where the oligo encodes a number of symbols corresponding to user data in the data unit; determining a plurality of reference marks, where at least one set of reference marks in the plurality of reference marks encodes an oligo index; inserting the plurality of reference marks at a predetermined interval along a length of the oligo, where the predetermined interval equals a fixed data length between sequential reference marks; and outputting write data for the oligo for synthesis of the oligo.

Implementations may include one or more of the following features. The predetermined interval of the plurality of reference marks may correspond to a single base pair between sequential reference marks. The oligo index may include an oligo address and a cyclic redundancy check code. The plurality of reference marks may include a plurality of copies of the oligo index; each copy of the oligo index may include a different set of reference marks of the at least one set of reference marks; and at least two copies of the oligo index may include different translations of the oligo index that order the corresponding sets of reference marks in different translation orders. Each copy of the oligo index may occupy a predetermined set of positions in the plurality of reference marks and have a known translation order for that predetermined set of positions and corresponding set of reference marks. The different translation orders may be selected from mirror symmetry and translational symmetry using circular offset values less than a length of the oligo index. The plurality of reference marks may include a reference number of base pairs in the oligo; the reference number of base pairs is a multiple of the length of the oligo index; the multiple may be at least equal to a number of the plurality of copies; and the number of the plurality of copies may be at least four. The different sets of reference marks of the at least two copies may be interleaved along the length of the oligo index. The method may include: receiving read data determined from sequencing the oligo; determining, from the read data, a convolutional matrix for the oligo, where each column of the convolutional matrix corresponds to a base pair offset of the read data for the oligo; determining, from the read data, a first reference matrix based on a first sequence of reference positions at an encoded frequency of the plurality of reference marks; determining, from the read data, a second reference matrix based on a second sequence of reference positions at the encoded frequency of the plurality of reference marks; determining a first correlation matrix based on a comparison of the convolutional matrix to the first reference matrix; determining a second correlation matrix based on a comparison of the convolutional matrix and the second reference matrix; determining a most likely path through a combination of the first correlation matrix and the second correlation matrix based on: a series of probabilities of moving between corresponding rows in the first correlation matrix and the second correlation matrix; and loop decoding for different symmetries of the plurality of copies of the oligo index; and decoding the oligo index based on the most likely path and the plurality of copies of the oligo index. The method may include: receiving, based on oligos with a same decoded oligo index, read data determined from sequencing at least two copies of the oligo; populating a reference mark correlation matrix based on a comparison of reference mark positions in a first copy of the oligo to reference mark positions in a second copy of the oligo; determining a most likely path through the reference mark correlation matrix corresponding to offset values for the plurality of reference marks; determining, based on at least one offset value for the plurality of reference marks, an insertion or deletion in a data segment between sequential reference marks; and correcting symbol alignment in the data segment to compensate for the insertion or deletion; and decoding the user data from the read data using an error correction code and corresponding redundancy data; and outputting, based on the decoded user data, the data unit.

Yet another general aspect includes a system that includes: means for determining an oligo for encoding a data unit, where the oligo encodes a number of symbols corresponding to user data in the data unit; means for determining a plurality of reference marks, where at least one set of reference marks in the plurality of reference marks encodes an oligo index; means for inserting the plurality of reference marks at a predetermined interval along a length of the oligo, where the predetermined interval equals a fixed data length between sequential reference marks; and means for outputting write data for the oligo for synthesis of the oligo.

The present disclosure describes various aspects of innovative technology capable of applying embedded reference marks that include copies of the oligo index for that oligo and traversing resulting correlation matrices using Viterbi algorithms to the encoding and decoding of user data stored in a DNA oligo pool. The configuration of reference marks and insertion/deletion error processing provided by the technology may be applicable to a variety of computer systems used to store or retrieve data stored as a set of oligos in a DNA storage medium. The configuration may be applied to a variety of DNA synthesis and sequencing technologies to generate write data for storage as base pairs and process read data read from those base pairs. The novel technology described herein includes a number of innovative technical features and advantages over prior solutions, including, but not limited to, improved data recovery based on elimination of insertion and deletion errors prior to applying other data recovery techniques (such as error correction codes and/or data correlation) to the insertion/deletion corrected user data.

DETAILED DESCRIPTION

Novel data storage technology is being developed to use synthesized DNA encoded with binary data for long-term data storage. While current approaches may be limited by the time it takes to synthesize and sequence DNA, the speed of those systems is improving and the density and durability of DNA as a data storage medium is compelling. In an example configuration in FIG. 1A, a method 100 may be used to store and recover binary data from synthetic DNA.

At block 110, binary data for storage to the DNA medium may be determined. For example, any conventional computer data source may be targeted for storage in a DNA medium, such as data files, databases, data objects, software code, etc. Due to the high storage density and durability of DNA media, the data targeted for storage may include very large data stores having archival value, such as collections of image, video, scientific data, software, enterprise data, and other archival data.

At block 112, the binary data may be converted to DNA code. For example, a convention computer data object or data file may be encoded according to a DNA symbol index, such as: A or T=1 and C or G=0; A=00, T=01, C-10, and G=11; or a more complex DNA symbol index mapping sequences of DNA bases to predetermined binary data patterns. In some configurations, prior to conversion to DNA code, the source data may be encoded according to an oligo-length format that includes addressing and redundancy data for use in recovering and reconstructing the source data during the retrieval process.

At block 114, DNA may be synthesized to embody the DNA code determined at block 112. For example, the DNA code may be used as a template for generating a plurality of synthetic DNA oligos embodying that DNA code using various DNA synthesis techniques. In some configurations, a large data unit is broken into segments matching a payload capacity of the oligo length being used and each segment is synthesized in a corresponding DNA oligo. In some configurations, solid-phase DNA synthesis may be used to create the desired oligos. For example, each desired oligo may be built on a solid support matrix one base at a time to match the desired DNA sequence, such as using phosphoramidite synthesis chemistry in a four-step chain elongation cycle. In some configurations, column-based or microarray-based oligo synthesizers may be used.

At block 116, the DNA medium may be stored. For example, the resulting set of DNA oligos for the data unit may be placed in a fluid or solid carrier medium. The resulting DNA medium of the set of oligos and their carrier may then be stored for any length of time with a high-level of stability (e.g., DNA that is thousands of years old had been successfully sequenced). In some configurations, the DNA medium may include wells of related DNA oligos suspended in carrier fluid or a set of DNA oligos in a solid matrix that can themselves be stored or attached to another object. A set of DNA oligos stored in a binding medium may be referred to as a DNA storage medium for an oligo pool. The DNA oligos in the pool may relate to one or more binary data units comprised of user data (the data to be stored prior to encoding and addition of syntactic data, such as headers, addresses, reference marks, etc.).

At block 118, the DNA oligos may be recovered from the stored medium. For example, the oligos may be separated from the carrier fluid or solid matrix for processing. The resulting set of DNA oligos may be transferred to a new solution for the sequencing process or may be stored in a solution capable of receiving the other polymerase chain reaction (PCR) reagents.

At block 120, the DNA oligos may be sequenced and read into a DNA data signal corresponding to the sequence of bases in the oligo. For example, the set of oligos may be processed through PCR to amplify the number of copies of the oligos from the stored set of oligos. In some configurations, PCR amplification may result in a variable number of copies of each oligo.

At block 122, a data signal may be read from the sequenced DNA oligos. For example, the sequenced oligos may be passed through a nanopore reader to generate an electrical signal corresponding to the sequence of bases. In some configurations, each oligo may be passed through a nanopore and a voltage across the nanopore may generate a differential signal with magnitudes corresponding to the different resistances of the bases. The analog DNA data signal may then be converted back to digital data based on one or more decoding steps, as further described with regard to a method 130 in FIG. 1B. Improved systems and methods for processing read data from the sequenced oligos to recover the data encoded in the original oligo, including both address/index data and user data, are further described with regard to FIGS. 2-7.

Figure 1B:
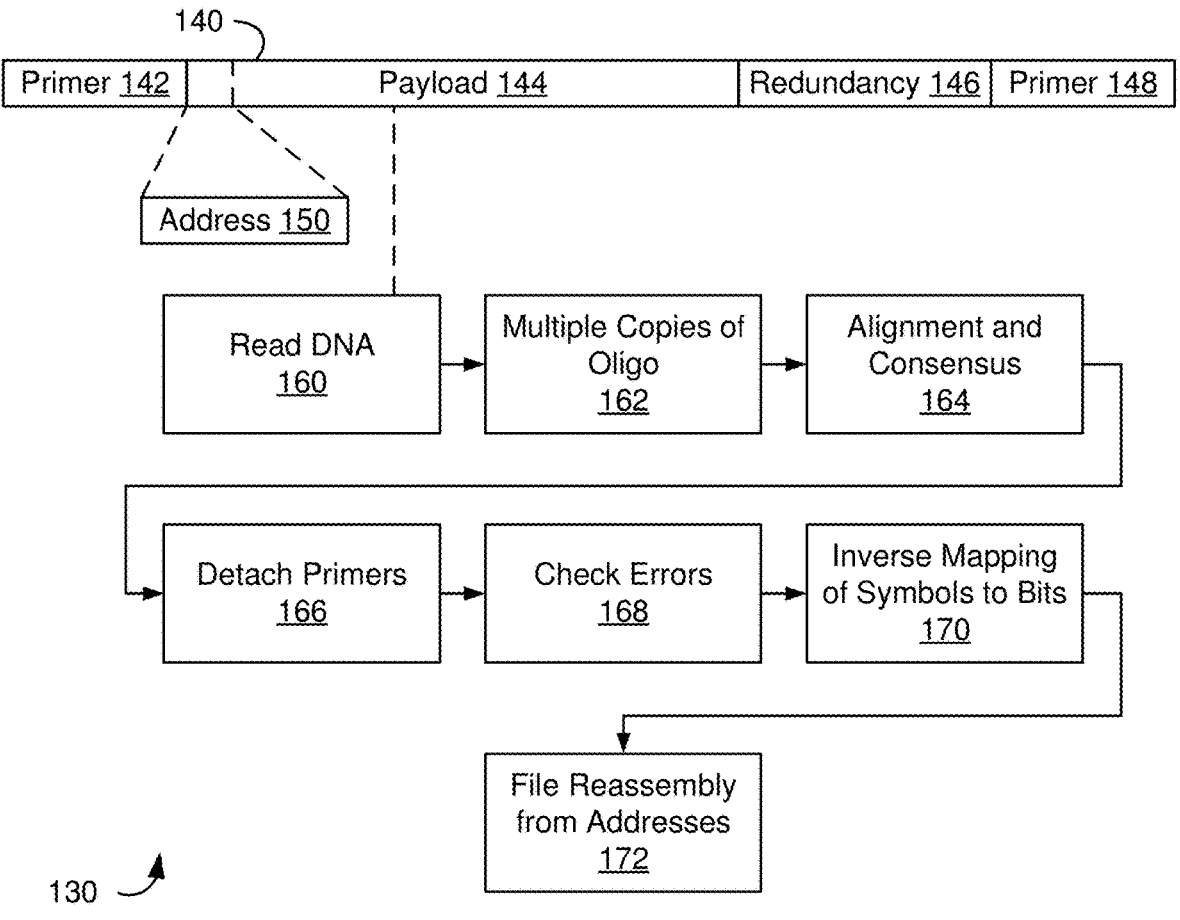
FIG. 1B is a block diagram of a prior art DNA data storage decoding process for oligos encoded with binary data.

In FIG. 1B, method 130 may be used to convert an analog read signal corresponding to a sequence of DNA bases back to the digital data unit that was the original target of the DNA storage process. In the example shown, the original digital data unit, such as a data file, was broken into data subunits corresponding to a payload size of the oligos and the set of oligos corresponding to the subunits of the data unit may be reassembled into the original data unit. An example oligo format 140, including primers 142 and 148 that may be added to support the PCR amplification and sequencing, may include a payload 144 comprising a sub-unit of the data unit, a redundancy portion 146 for error correction code (ECC) data for that subunit, and an address portion 150 for determining the sequence of the payloads for reassembling the data block. In some configurations, Reed-Solomon error correction codes may be used to determine the redundancy portion 146 for payload 144.

At block 160, DNA base data signals may be read from the sequenced DNA. For example, the analog signal from the nanopore reader may be conditioned (equalized, filtered, etc.) and converted to a digital data signal for each oligo.

At block 162, multiple copies of the oligos may be determined. Through the amplification process, multiple copies of each oligo may be produced and the decoding system may determine groups of the same oligo to process together.

At block 164, each group of the same oligo may be aligned and consensus across the multiple copies may be determined. For example, a group of four copies may be aligned based on their primers and each base position along the set of base values may have a consensus algorithm applied to determine a most likely version of the oligo for further processing, such as, where 3 out of 4 agree, that value is used.

At block 166, the primers may be detached. For example, primers 142 and 148 may be removed from the set of data corresponding to payload data 144, redundancy data 146, and address 150.

At block 168, error checking may be performed on the resulting data set. For example, ECC processing of payload 144 based on redundancy data 146 may allow errors in the resulting consensus data set for the oligo to be corrected. The number of correctable errors may depend on the ECC code used. ECC codes may have difficulty correcting errors created by insertions or deletions (resulting in shifts of all following base values). The size of the oligo payload 144 and portion allocated to redundancy data 146 may determine and limit the correctable errors and efficiency of the data format.

At block 170, the bases or base symbols may be inversely mapped back to the original bit data. For example, the symbol encoding scheme used to generate the DNA code may be reversed to determine corresponding sequences of bit data.

At block 172, a file or similar data unit may be reassembled from the bit data corresponding to the set of oligos. For example, address 150 from each oligo payload may be used to order the decoded bit data and reassemble the original file or other data unit.

Figure 2:
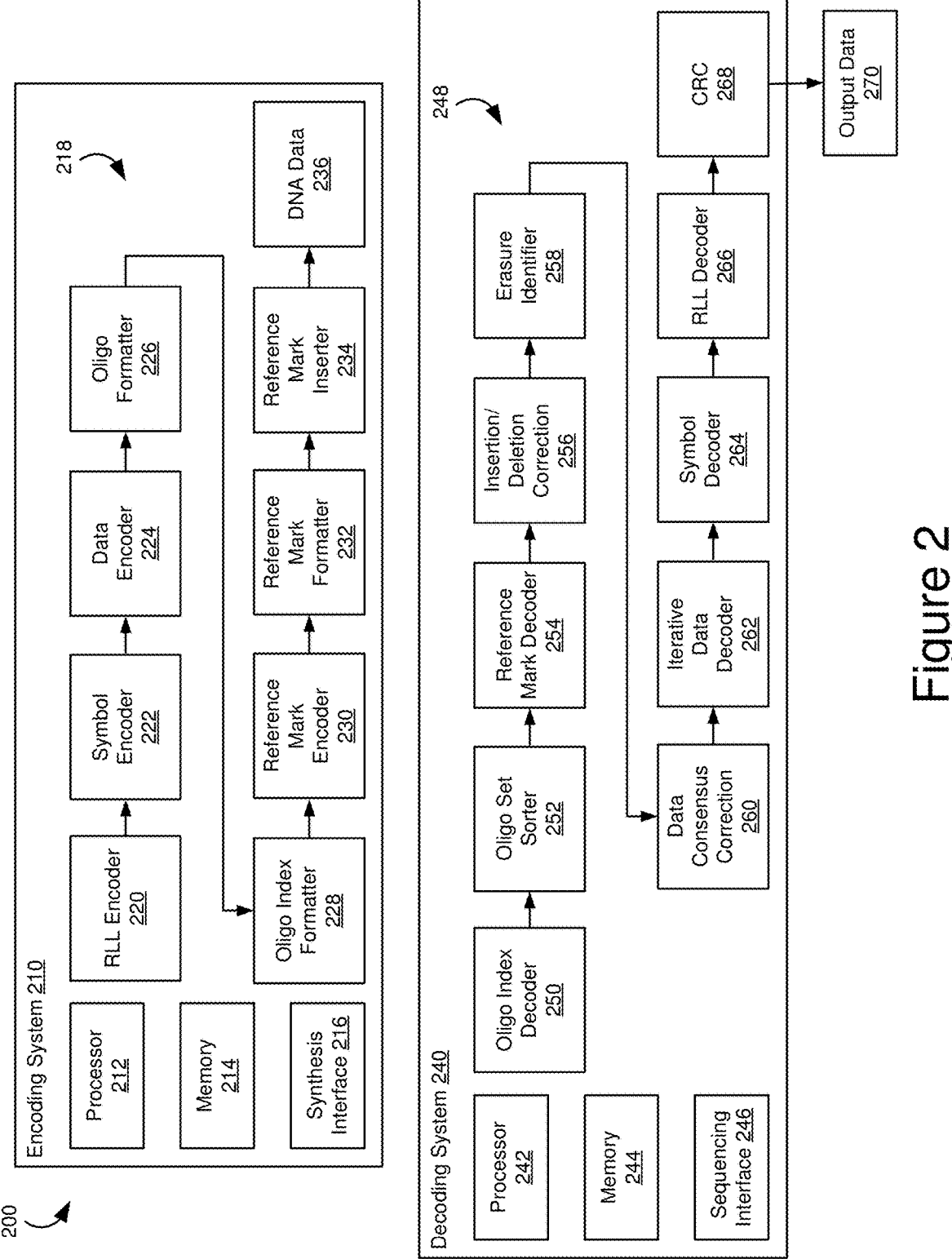
FIG. 2 is a block diagram of an example encoding system and example decoding system for DNA data storage using reference marks to store the oligo index.

FIG. 2 shows an improved DNA storage system 200 and, more specifically, an improved encoding system 210 and decoding system 240 for using multistage error correction using reference marks to correct for insertion/deletion errors before applying other error correction techniques to address mutation and/or erasure errors. In some configurations, encoding system 210 may be part of a first computer or storage system or device used for determining target binary data, such as a conventional binary data unit, and converting it to a DNA base sequence for synthesis into DNA for storage and decoding system 240 may be part of a second computer or storage system or device used for receiving the data signal corresponding to the base sequence read from the DNA.

Encoding system 210 may include a processor 212, a memory 214, and a synthesis system interface 216. For example, encoding system 210 may be part of a computer or storage system or device configured to receive or access conventional computer data, such as data stored as binary files, blocks, data objects, databases, etc., and map that data to a sequence of DNA bases for synthesis into DNA storage units, such as a set of DNA oligos. Processor 212 may include any type of conventional processor or microprocessor that interprets and executes instructions. In some configurations, processor 212 may include a plurality of processors or processor cores configured to operate alone or in combination to execute one or more functions or sets of instructions described with regard to the other components of encoding system 210. Memory 214 may include a random-access memory (RAM) or another type of dynamic storage device that stores information and instructions for execution by processor 212 and/or a read only memory (ROM) or another type of static storage device that stores static information and instructions for use by processor 212. In some configurations, one or more components of encoding system 210 may be embodied in specialized logic and memory circuits configured for the functions described for encoding system 210 and may incorporate or operating in conjunction with processor 212 and memory 214. For example, one or more encoders, formatters, and/or insertion functions may be embodied in a specialized circuit, such as a system on a chip (SOC), field programmable gate array (FPGA), application specific integrated circuit (ASIC), or similar circuit configuration. Encoding system 210 may also include any number of input/output devices and/or interfaces. Input devices may include one or more conventional mechanisms that permit an operator to input information to encoding system 210, such as a keyboard, a mouse, a pen, voice recognition and/or biometric mechanisms, etc. Output devices may include one or more conventional mechanisms that output information to the operator, such as a display, a printer, a speaker, etc. Interfaces may include any transceiver-like mechanism that enables encoding system 210 to communicate with other devices and/or systems. For example, synthesis interface 216 may include a connection to an interface bus (e.g., peripheral component interface express (PCIe) bus) or network for communicating the DNA base sequences for storing the data to a DNA synthesis system. In some configurations, synthesis system interface 216 may include a network connection using internet or similar communication protocols to send a conventional data file listing the DNA base sequences for synthesis, such as the desired sequence of bases for each oligo to be synthesized, to the DNA synthesis system. In some configurations, the DNA base sequence listing may be stored to conventional removable media, such as a universal serial bus (USB) drive or flash memory card, and transferred from encoding system 210 to the DNA synthesis system using the removable media.

In some configurations, a series of processing components 218 may be used to process the target binary data, such as a target data file or other data unit, into the DNA base sequence listing for output to the synthesis system. For example, processing components 218 may be embodied in encoder software and/or hardware encoder circuits. In some configurations, processing components 218 may be embodied in one or more software modules stored in memory 214 for execution by processor 212. Note that the series of processing components 218 are examples and different configurations and ordering of components may be possible without materially changing the operation of processing components 218. For example, in an alternate configuration, additional data processing, such as a data randomizer to whiten the input data sequence, may be used to preprocess the data before encoding. In another configuration, user data from a target data unit may be divided across a set of oligos according to oligo payload size or other data formatting prior to applying any encoding or sync marks may be added after ECC encoding. Other variations are possible.

In some configurations, processing the target data may begin with a run length limited (RLL) encoder 220. RLL encoder 220 may modulate the length of stretches in the input data. RLL encoder 220 may employ a line coding technique that processes arbitrary data with bandwidth limits. Specifically, RLL encoder 220 may bound the length of stretches of repeated bits or specific repeating bit patterns so that the stretches are not too long or too short. By modulating the data, RLL encoder 220 can reduce problematic data sequences that could create additional errors in subsequent encoding and/or DNA synthesis or sequencing. In some configurations, RLL encoder 220 or a similar data modulation component may be configured to modulate the input data to assure that data patterns used for syntax references do not appear elsewhere in the user data encoded in the oligo.

In some configurations, symbol encoder 222 may include logic for converting binary data into symbols based on the four DNA bases (adenine (A), cytosine (C), guanine (G), and thymine (T)). In some configurations, symbol encoder 222 may encode each bit as a single base pair, such as 1 mapping to A or T and 0 mapping to G or C. In some configurations, symbol encoder 222 may encode two-bit symbols into single bases, such as 11 mapping to A, 00 mapping to T, 01 mapping to G, and 10 mapping to C. More complex symbol mapping can be achieved based on multi-base symbols mapping to correspondingly longer sequences of bit data. For example, a two-base symbol may correspond to 16 states for mapping four-bit symbols or a four-base symbol may map the 256 states of byte symbols. Multi-base pair symbols could be preferable from an oligo synthesis point of view. For example, synthesis could be done not on base pairs but on lager blocks, like 'bytes' correlating to a symbol size, which are prepared and cleaned up earlier (e.g., pre-synthesized) in the synthesis process. This may reduce the amount of synthesis errors. From an encoder/decoder point of view, these physically larger blocks could be treated as symbols or a set of smaller symbols.

In some configurations, data encoder 224 may include logic for encoding the user data unit using one or more error correction schemes and may encode user data units across multiple oligos. For example, encoding system 210 may use low-density parity check (LDPC) codes constructed for the oligo size and/or larger codewords than can be written to a single oligo. In some configurations, data across multiple oligos may be aggregated to form the desired codewords. Similarly, parity or similar redundancy data may not need to be written to each oligo and may instead be written to only a portion of the oligos or written to separate parity oligos that are added to the oligo set for the target data unit. In some configurations, ECC encoding may then be nested for increasingly aggregated sets of oligos, where each level of the nested ECC corresponds to increasingly larger codewords comprised of more oligos. Encoding system 210 may include one or more oligo aggregators and corresponding iterative encoders. For example, single level ECC encoding may use first level oligo aggregator and first level iterative encoder for codewords of 200-400 oligos. A two-level encoding scheme would use first and second level oligo aggregators for and corresponding first and second level iterative encoders, such as for 200 oligo codewords at the first level and 4000 oligo codewords at the second level.

Data encoder 224 may append one or more parity bits to the sets of codeword data for later detection whether certain errors occur during data reading process. For instance, an additional binary bit (a parity bit) may be added to a string of binary bits that are moved together to ensure that the total number of "1"s in the string is even or odd. The parity bits may thus exist in two different types, an even parity in which a parity bit value is set to make the total number of "1"s in the string of bits (including the parity bit) to be an even number, and an odd parity in which a parity bit is set to make the total number of "1"s in the string of bits (including the parity bit) to be an odd number. In some examples, data encoder 224 may implement a linear error correcting code, such as LDPC codes or other turbo codes, to generate codewords that may be written to and more reliably recovered from the DNA medium. In some configurations, resulting parity or similar redundancy data may be stored in parity oligos designated to receive the redundancy data for the set of oligos that make up the codeword data. This additional parity data may be encoded using RLL encoder 220, symbol encoder 222, oligo formatter 226, and/or reference mark logic.

In some configurations, oligo formatter 226 may include logic for allocating portions of the target data unit to a set of oligos. For example, oligo formatter 226 may be configured for a predetermined payload size for each oligo and select a series of symbols corresponding to the payload size for each oligo in the set. In some configurations, the payload size may be determined based on an oligo size used by the synthesis system and any portions of the total length of the oligo that are allocated to redundancy data, address data, reference mark data, or other data formatting constraints. For example, for a 150 base pair oligo using two-base symbols may include an eight-base addressing scheme and six four-base sync marks, resulting in 118 base pairs of the target data allocated to each oligo. In some configurations, oligo formatter 226 may insert a unique oligo address or oligo index (including the oligo address) for each oligo in the set, such as at the beginning or end of the data payload. The oligo address may allow the encoding and decoding systems to identify the data unit and relative position of the symbols in a particular oligo relative to the other oligos that contribute data to that data unit. For example, decoding system 240 may use position information corresponding to the oligo addresses to reassemble the data unit from a set of oligos in an oligo pool containing one or more data units. In some configurations, rather that including the oligo index in a data sequence separate from the user data payload, such as a header or footer of the oligo data, the oligo index may be embedded or encoded in the reference marks distributed through the data payload. This may allow the reference marks to double as oligo index space, reducing overall data overhead, and allow for redundant copies of the oligo index to be more reliably encoded in the oligo.

In some configurations, oligo index formatter 228 may include logic to assemble the oligo index data to be included in the oligo. In prior oligo data formats, oligo index formatter 228 may operate as part of oligo formatter 226 to collect and format the oligo index data for the sequence of base pairs that would store the index, such as a specific set of base pairs within the oligo header. In configurations that embed the oligo index in a distributed fashion, such as embedded within the sequence of reference marks, oligo index formatter 228 may operate separately from oligo formatter 226 to conform with the reference mark format determined by reference mark encoder 230, reference mark formatter 232, and reference mark inserter 234. Oligo index formatter 228 may determine a sequence or set of base pairs that correspond to the oligo index data, such as the oligo address, one or more other syntactical parameters, and/or encoding specific to the oligo index (e.g., oligo index CRC or parity bits). In some configurations, the oligo index data may include only the oligo address. The set of data for the oligo index may be determined and encoded as a sequence of base pairs that may form the basis of the reference mark sequence.

In some configurations, reference mark encoder 230 may include logic for determining a pattern of values to be used for reference marks. For example, a series of base pairs placed at rigid, predetermined intervals or frequency may conform to a known sequence for detecting the presence of the reference marks interspersed with user data over the length of the oligo. In some configurations, each reference mark may be a single base pair and, thus, would not be inherently distinguishable from user data encoded using that base pair. However, when aggregated across a series or set of reference marks, the reference marks may be identified as syntactic references separate from the user data they provide a reference for. By using a rigid interval or frequency of a fixed number of user data base pairs between reference mark base pairs, a pattern similar to the timing structure used in the reading and writing of moving media, such as rotating magnetic/optical disks or linear magnetic tapes, may be established. In some configurations, similar encoding and logics from timing marks in moving media may be used for reference marks. For example, a convolutional code, including hash encoded decoded by greedy exhaustive search (HEDGES) ECC, that is configured for detection and recovery across a series of reference marks may be selected. In some configurations, reference mark encoder 230 may include a cyclic redundancy check (CRC) code that may be used to verify the sequence in the reference marks during the decoding process.

In some configurations, reference mark encoder 230 may operate on the oligo index data set received from oligo index formatter 228. For example, the oligo index data may be modulated and encoded using a convolutional code to be reliable distinguished from the user data as reference marks during decoding. That is the oligo index data may form the basis of the reference mark pattern and reference mark encoder 230 may be configured to receive and encode the oligo index data set for generation of the reference marks. In some configurations, the number of base pairs committed to reference marks across the length of the oligo may be greater than the size of the oligo index data set. For example, the oligo index may be sized such that multiple copies of the oligo index may be redundantly stored across the base pairs in the reference marks. The reference marks may provide space for two or more copies of the oligo index and, in some configurations, four or more copies. Reference mark encoder 230 may provide the encoded oligo index to reference mark formatter 232 for determining the configuration of the multiple copies to be stored across the reference marks.

In some configurations, reference mark formatter 232 may include logic for formatting reference marks for insertion at predetermined intervals among the data symbols. For example, reference marks may be inserted every X base pairs to divide the data in the oligo into a predetermined number of shorter data segments with a timing frequency of 1/X and a resulting code rate of 1/(X+(base pairs in each reference mark). In some configurations, each reference mark may comprise a single base pair as described for reference mark encoder 230 for a code rate of 1/(X+1). In some configurations, a code rate of 0.5 (1/(1+1), alternating a base pair of user data with a base pair reference mark) may be selected to provide a desired likelihood of reference recovery and a high likelihood of identifying and correcting insertion and deletion errors to return the user data to a desired timing/data pattern with only mutation and/or erasure errors to be addressed through user data ECC. In an example configuration, an oligo may have a payload space of 140 base pairs and, formatting the reference marks at a 0.5 code rate would result in 70 base pairs of user data alternating with 70 base pairs of reference marks. The predetermined sequence and frequency of the reference marks may be used during the decoding process to determine and evaluate user data segments within an oligo to better detect and localize insertions and deletions that are difficult for error correction codes to detect or correct. For example, decoding system 240 may detect reference marks and correct symbol alignment prior to attempting iterative decoding with ECC. Use of reference marks is further described below with regard to decoding system 240 and FIGS. 3-7.

Figure 3A:
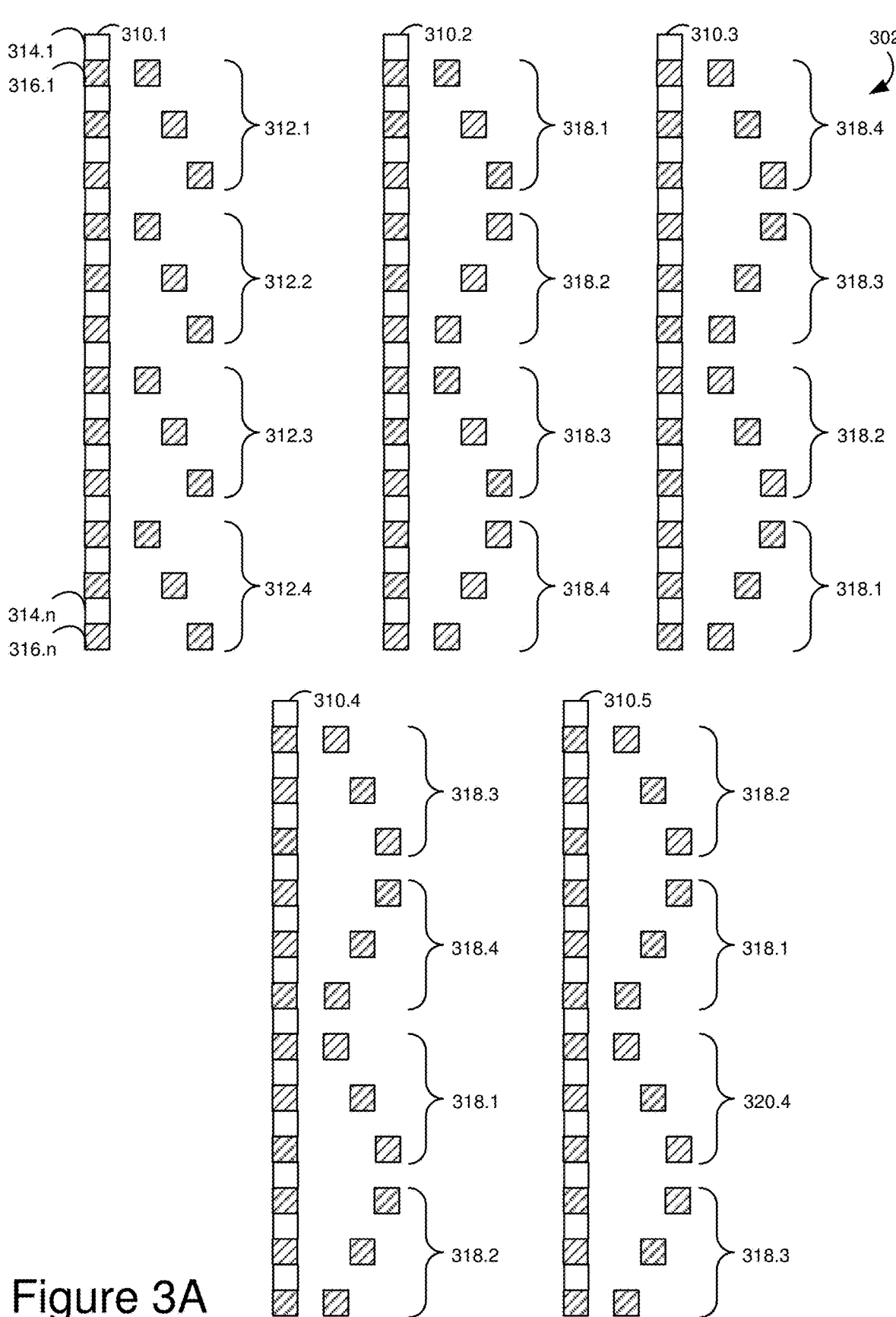
FIGS. 3A, 3B, and 3C are diagrams of oligo processing to recover the oligo index from the reference marks in oligo read data.

Reference mark formatter 232 may be configured to determine the number of copies and configuration of those copies of the encoded reference mark pattern. For example, where the reference mark pattern is based on the oligo index data set, reference mark formatter 232 may determine the number of copies and the positions and/or translations of those copies across the reference marks. As shown in FIG. 3A, an example set of oligo data 310.1 may be include user data base pairs 314.1-314.$n$ alternating with reference mark base pairs 316.1-316.$n$. In the example shown, for simplicity, the oligo index comprises a base pair sequence 312 of three base pairs and the length of the oligo data sequence can accommodate four copies 312.1-312.4. In oligo data 310.1, the oligo index sequence 312 is simply repeated four times as copy 312.1, followed by copy 312.2, followed by copy 312.3, followed by copy 312.4, where each copy is identical in ordering. However, such translational symmetry, where the sequence is simply repeated, may undermine efforts to recover the reference marks and the oligo data due to the nature of DNA errors and reference mark encoding and recovery. It may be advantageous to introduce mirror symmetry between adjacent copies of the reference mark pattern or oligo index sequence. As shown for oligo data 310.2 in FIG. 3A, the order of oligo index sequence 318 may be mirrored to introduce mirror symmetry between adjacent copies. For example, copy 318.1 is mirrored by copy 318.2, copy 318.2 is mirrored by copy 318.3, and copy 318.3 is mirrored by copy 318.4. Oligo data 310.3 in FIG. 3A shows an alternate configuration where the adjacent copies are not only mirrored but the order of the copies along the length is also reversed. Copy 318.1 is shown at the end of oligo data 310.3 and copy 318.4 is at the start of oligo data 310.3. The mirror symmetry of adjacent copies is similar to oligo data 310.2 but the ordering of the reference marks as a whole are mirrored from oligo data 310.2. Further variation in the sequence of copies may be introduced through circular shifts and combinations of mirroring and circular shifts. For example, in oligo data 310.4 the mirrored copies are then circular shifted by two positions such that oligo data 310.4 includes copies 318.3 and 318.4 in the front positions and copies 318.1 and 318.2 in the end positions. In oligo data 310.5, the mirrored order from 310.3 has been circular shifted by two copies such that copies 318.2 and 318.1 are in the front positions and copies 318.4 and 318.3 are in the end positions. Reference mark formatter 232 may be configured to determine the combinations of mirroring and circular shifts to employ when ordering multiple copies of the oligo index data along the length of the oligo.

In some configurations, reference mark inserter 234 may include logic to insert the sequence of reference marks into the user data for determining the DNA sequence to be synthesized. For example, reference mark inserter 234 may operate according to the frequency configured in reference mark formatter 232 to insert the sequence of base pairs determined by reference mark encoder 230 and ordered copies from reference mark formatter 232 between corresponding portions of the user data. In the example using a code rate of 0.5, reference mark inserter 234 may alternate selecting a next base pair from the encoded user data with a next base pair from the reference marks to interleave single base pairs of user data with single base pair reference marks. In other configurations, a single base pair reference mark may be inserted after a plurality of user data base pairs, such as a larger (multi-base pair) symbol or segment size.

The resulting DNA base pair sequence corresponding to the encoded target data unit may be output from processing components 218 as DNA data 236. For example, the base pair sequences for each oligo in the set of oligos corresponding to the target data unit may be stored as sequence listings for transfer to the synthesis system. In some configurations, the base pair sequences may include the encoded data unit data formatted for each oligo, including address, sync mark, and redundancy data added to the user data for the data unit. The set of oligos may include a plurality of first level codeword sets and their corresponding parity oligos and, in some configurations, nested groups of first level codeword sets, second level codeword sets, and so on for as many levels as the particular recovery configuration supports.

Decoding system 240 may include a processor 242, a memory 244, and a sequencing system interface 246. For example, decoding system 240 may be part of a computer or storage system or device configured to receive or access analog and/or digital signal read data from reading sequenced DNA, such as the data signals associated with a set of oligos that have been amplified, sequenced, and read from stored DNA media. Processor 242 may include any type of conventional processor or microprocessor that interprets and executes instructions. In some configurations, processor 242 may include a plurality of processors or processor cores configured to operate alone or in combination to execute one or more functions or sets of instructions described with regard to the other components of encoding system 210. Memory 244 may include a random-access memory (RAM) or another type of dynamic storage device that stores information and instructions for execution by processor 242 and/or a read only memory (ROM) or another type of static storage device that stores static information and instructions for use by processor 242. In some configurations, one or more components of encoding system 210 may be embodied in specialized logic and memory circuits configured for the functions described for encoding system 210 and may incorporate or operating in conjunction with processor 212 and memory 214. For example, one or more encoders, formatters, and/or insertion functions may be embodied in a specialized circuit, such as a system on a chip (SOC), field programmable gate array (FPGA), application specific integrated circuit (ASIC), or similar circuit configuration. Decoding system 240 may also include any number of input/output devices and/or interfaces. Input devices may include one or more conventional mechanisms that permit an operator to input information to decoding system 240, such as a keyboard, a mouse, a pen, voice recognition and/or biometric mechanisms, etc. Output devices may include one or more conventional mechanisms that output information to the operator, such as a display, a printer, a speaker, etc. Interfaces may include any transceiver-like mechanism that enables decoding system 240 to communicate with other devices and/or systems. For example, sequencing system interface 246 may include a connection to an interface bus (e.g., peripheral component interface express (PCIe) bus) or network for receiving analog or digital representations of the DNA sequences from a DNA sequencing system. In some configurations, sequencing system interface 246 may include a network connection using internet or similar communication protocols to receive a conventional data file listing the DNA base sequences and/or corresponding digital sample values generated by analog-to-digital sampling from the sequencing read signal of the DNA sequencing system. In some configurations, the DNA base sequence listing may be stored to conventional removable media, such as a universal serial bus (USB) drive or flash memory card, and transferred to encoding system 240 from the DNA sequencing system using the removable media.

In some configurations, a series of processing components 248 may be used to process the read data, such as a read data file or read data signal from a DNA sequencing system, to output a conventional binary data unit, such as a computer file, data block, or data object. For example, processing components 248 may be embodied in decoder software and/or hardware decoder circuits. In some configurations, processing components 248 may be embodied in one or more software modules stored in memory 244 for execution by processor 242. Note that the series of processing components 248 are examples and different configurations and ordering of components may be possible without materially changing the operation of processing components 248. For example, in an alternate configuration, additional data processing for reversing modulation or other processing from encoding system 216 and/or reassembly of decoded oligo data into larger user data units may be included. Other variations are possible.

Decoding system 240 may use a first stage of error correction targeting the elimination of insertion and deletion errors (which create shifts in all following base pairs in a sequence), followed by ECC error correction to address mutation or erasure errors. DNA media and sequencing face three main types of errors: deletion, insertion, and mutation. Mutation errors are most similar to the traditional errors in data storage and may efficiently be handled using ECC correction. Insertion and deletion errors affect the position of all following bits or symbols and may not be effectively handled by ECC. Therefore, preprocessing the oligo sequences for sequence position shifts and, where possible, correcting those position shifts may contribute to more efficient and reliable data reading. The preprocessing stage may reduce the error rate in the oligo sequences significantly prior to applying ECC correction, enabling more efficient ECC codes and more reliable retrieval of data using a first level of ECC encoding in nested ECC configurations. In some configurations, the preprocessing stage may include oligo index decoder 250, oligo set sorter 252, reference mark decoder 254, insertion/deletion correction 256, and erasure identifier 258.

In some configurations, oligo index decoder 250 may include logic to determine an oligo index from the read data of one or more oligo copies. For example, the oligo index may be included in a header or footer, distributed in multiple locations, or otherwise located in a known position in the oligo. The oligo index may include oligo and/or data unit identifiers or addresses used by decoding system 240 to identify where the user data in the oligo fits in a larger structure of user data, such as data unit or segment identifier for a file or data object. In some configurations, the oligo index may include additional syntactic data related to oligo formatting and/or ECC. Each oligo (and corresponding read data) may include an oligo index and correct identification and decoding of the oligo index may be an important element in correctly recovering the user data in the oligo and/or a larger data unit of which that data is a part. The oligo index may be encoded in its own data format and include its own ECC, such as parity data and/or CRC codes.

Figure 3B:
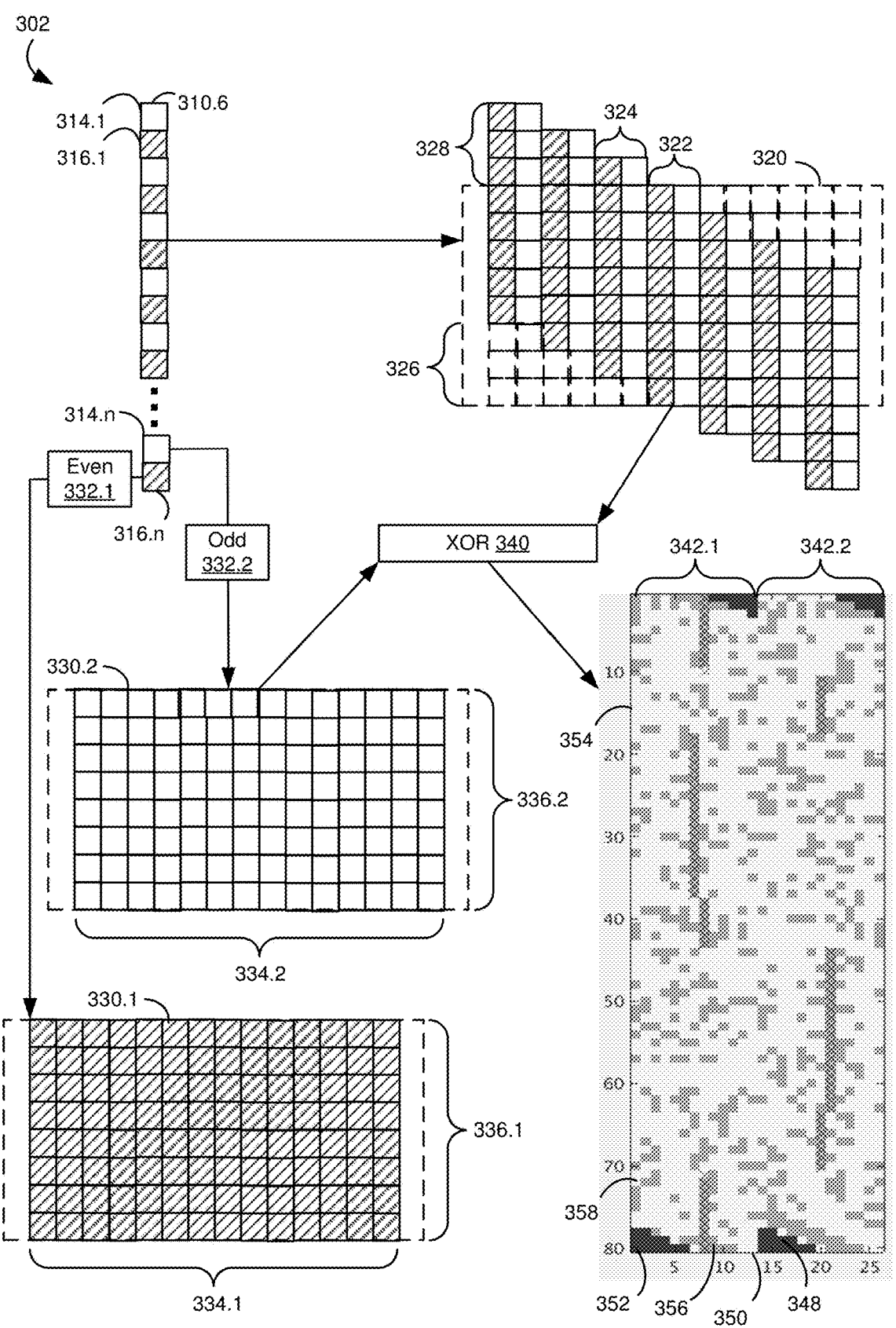

In some configurations, oligo index decoder 250 may include logic to determine the oligo index from the reference marks distributed through the oligo read data. For example, the read data for each oligo may include reference marks interspersed with the user data and the oligo index data may be encoded in one or more sequences of the reference marks. In some configurations, oligo index decoder 250 may be configured to operate on a single copy of oligo read data and reliably determine the oligo index data from the set of reference marks using a correlation matrix to align the reference marks and multiple copies of the oligo index to determine the oligo index contents from consensus (across oligo index copies) and/or error correction. As shown in FIG. 3B, a series of operations 302 may generate and populate a correlation matrix based on oligo read data 310.6. In some configurations, read data 310.6 may be used to generate a convolutional matrix 320. Convolutional matrix 320 may be based on filtering and stacking reference mark positions 316.1-316.*n* and user data positions 314.1-314.*n* from the read data to make alternating columns of the respective base pairs. In the example shown, one base pair reference marks alternate with one base pair of user data, so filtering may be base6 on selecting the odd positions as user data values and the even positions as reference mark values. Each column includes a number of base pairs representing the user data portion or the reference mark portion of the oligo (e.g., half the length of the oligo for each type). The center pair of columns 322 comprise the full set of reference mark base pairs and user data base pairs. Each pair of columns in either direction is then offset by one row or base pair of that type (though this represents a two base pair offset when both reference marks and user data are considered). For example, columns 324 are offset by one row from columns 322. Where no read values are available due to the offset of the read data, placeholders 326 may be added. These are null values that are not valid portions of convolutional matrix 320 for subsequent calculations. Similarly, read data values 328 that fall outside of convolutional matrix 320 are not represented in the matrix and are shown merely for illustrating the data shift. The resulting convolutional matrix includes rows corresponding to pairs of positions along the oligo and the columns correspond to single base pair offsets that, if no insertion or deletion errors were present, would alternate between reference mark base pairs and user data base pairs.

In some configurations, read data 310.6 may also be used to generate a pair of reference matrices 330.1 and 330.2 based on the reference mark frequency and not knowing whether insertion or deletion errors may have misaligned some or all of the reference marks. Unlike convolutional matrix 320, reference matrices 330 are constructed without offset. An even filter 332.1 targeting the ideal reference mark positions may filter that set of base pairs and an odd filter 332.2 targeting the remaining data positions may filter that set of base pairs. For example, filters 332 may filter read data 310.6 at the reference mark frequency by selecting every other base pair starting with the first or second base pair. Each column 334.1 repeats the reference mark set of base pairs in reference matrix 330.1 and each column 334.2 repeats the remaining data set of base pairs in reference matrix 330.2. Each row 336 includes the same base pair values corresponding to that position in read data 310.6, even base pairs in rows 336.1 and odd base pairs in rows 336.2.

An exclusive-or (XOR) operation 340 may then be used to compare each base pair in convolutional matrix 320 with the corresponding matrix position in reference matrices 330.1 and 330.2. The results of this comparison may populate a correlation matrix 350. The comparisons to the two reference matrices 330.1 and 330.2 may result in two portions or pages 342.1 and 342.2 of correlation matrix 350 corresponding to the odd and even base pairs used to populate the reference matrices. Page 342.1 may correspond to the comparisons to reference matrix 330.1 and page 342.2 may correspond to the comparisons to reference matrix 330.2. The x-axis 352 denotes the columns of the correlation matrix. For each page 342.1 and 342.2, the central reference mark column from convolutional matrix 320 corresponds to 0 offset and each column to the left or right corresponds to a one base pair offset in that direction. In the example shown, a band of 6 offset positions in each direction is being used, with 7 being the nominal (encoded) position of the reference marks on page 342.1, 1 being a 6 base pair shift generally corresponding to the direction of deletions and 13 being a 6 base pair shift generally corresponding to the direction of insertions. The nominal position of reference marks on page 342.1 may be 20, 14 being a 6 base pair shift to the left and 26 being a 6 base pair shift to the right. The y-axis 354 denotes the rows of the correlation matrix and correspond to reference mark positions along the oligo. Medium gray positions, such as block 356, correspond to 0 or base pair matches from the XOR comparison. Light gray positions, such as block 358, correspond to 1 or base pair mismatches from the XOR comparison. Dark gray positions in the corners of the pages, such as block 348, correspond to the placeholder or null values that are outside the valid positions of the matrix (created by the data shifts in convolutional matrix 320). Correlation matrix 350 may be used to determine the most likely positions of insertions and deletions based on shifts in the matching values by one or more columns in each direction. Note that while convolutional matrix 320 and reference matrices 330.1 and 330.2 are graphically illustrated with a small number of oligo positions, example correlation matrix 350 is based on a more common oligo size of 160 base pairs, yielding 80 base pair positions corresponding to reference marks at a 0.5 code rate.

Figure 3C:
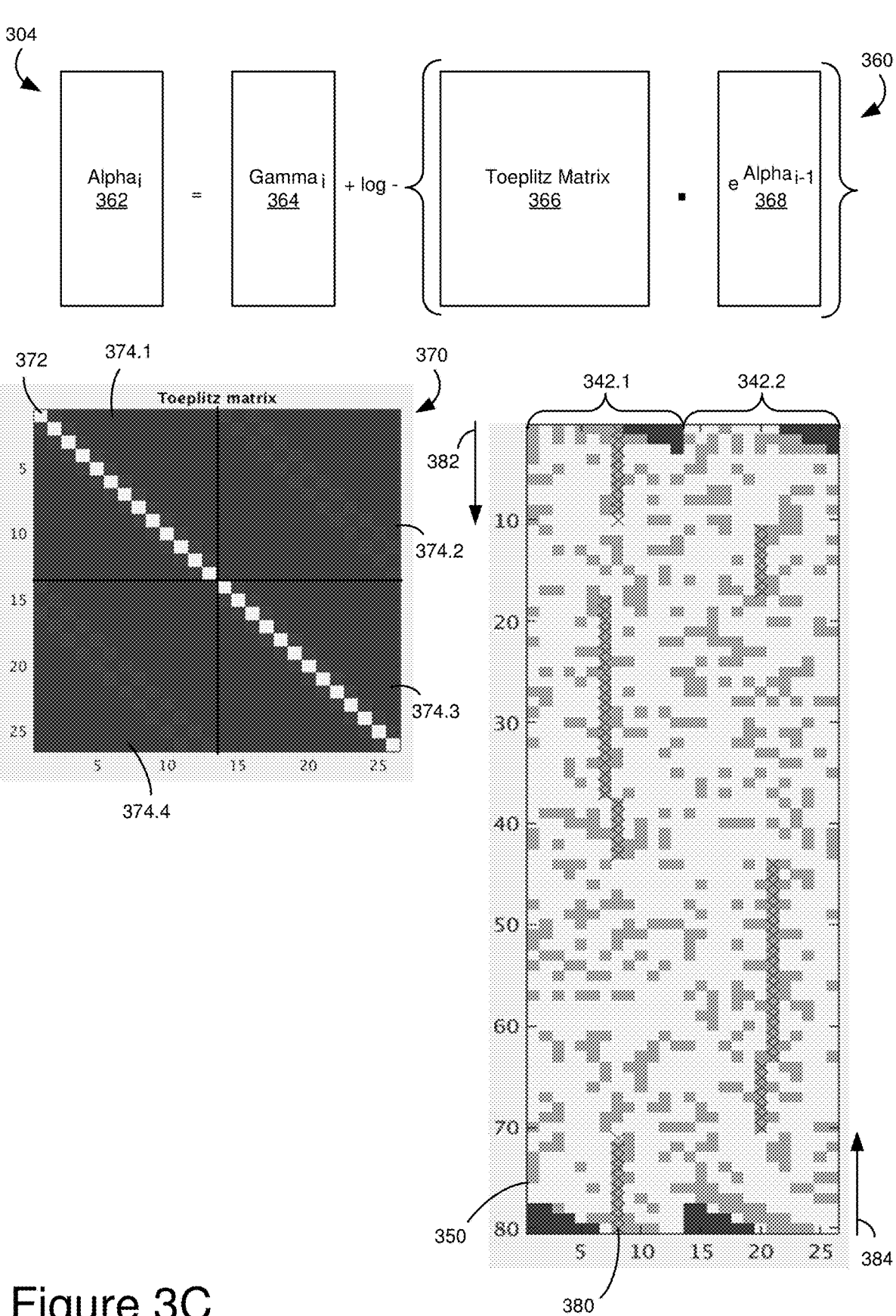

As shown in FIG. 3C, a sequence of operations 304 may use a Viterbi-like algorithm 360 to analyze correlation matrix 350 and identify the most likely path through the sequence of reference positions. The algorithm applies one or more traverses of the rows of correlation matrix 350 to determine whether the reference position has shifted due to an insertion or deletion. Based on the two-page configuration of correlation matrix 350, shifts may be identified as movement between pages 342.1 and 342.2, where a shift of one base pair left or right, moves the most likely path from one page to the other-corresponding to shifts between nominal reference positions and nominal data positions. In some configurations, algorithm 360 is a recursive Viterbi algorithm that uses the probability determined for a prior value in the matrix to determine the probability of the next value in the matrix in the direction of the traversal. $Alpha_i$ values 362 may include a set of values corresponding to the next row in correlation matrix 350 to be analyzed. $Gamma_i$ values 364 may correspond to a set of values for the column shift or offset of the next row. The offset values may be modified by a probabilistic term based on the log of the exponential function of the prior Alpha values 368 ($e^{Alpha_{i-1}}$) multiplied by a Toeplitz matrix 366. Toeplitz matrix 366 represents the probabilities of moving from one page to the other (insertions or deletions shifting reference mark alignment) and limits the probable movements to a desired range. An example Toeplitz matrix 370 comprises a central diagonal 372 corresponding to no shift—the light gray squares may represent constant values of 1. Toeplitz matrix 370 may further define quadrants corresponding to shifts between pages and may indicate a column shift when the most likely path switches pages. For example, quadrants 374.1 and 374.3 may correspond to paths into a page and quadrants 374.2 and 374.4 may correspond to jumps out of the page. In this context, paths into a page may shift to the corresponding column on the other page and jumps out of the page may shift one column in the transition to the other page. In Toeplitz matrix 370, shifts are limited to a single base pair shift by treating all adjacent diagonals outside of diagonal 372 as an indication to change pages (one base pair shift) and using the quadrants to determine the direction of the transition.

The output of Viterbi algorithm 360 may be a set of probabilities for each row, with the highest probability value indicating the most likely shift or offset for that position (or no shift/offset if the highest probability corresponds to the central reference mark column). In the example shown, indicator (x) 380 in each row corresponds to the column selected for that row as the most likely shift value based on the highest probability value for that row. In some configurations, Viterbi algorithm 360 may be evaluated in multiple directions and summed or averaged to determine the most likely values for each reference position (row). For example, a first direction 382 may correspond to traversing correlation matrix 350 from the top row (first reference mark position in the oligo) to the bottom row (last reference mark position in the oligo). A second direction 384 may correspond to traversing correlation matrix 350 in the reverse or opposite direction from the bottom row (last reference mark position in the oligo) to the top row (first reference mark position in the oligo). The results from the two traversals may then be summed or otherwise evaluated to determine the most likely shift for each reference mark position.

In some configurations, the Viterbi algorithm 360 may be executed iteratively in response to adjustments made to correct insertions and deletions until reference timing may be restored or the reference timing is determined to be unrecoverable. In some configurations, because the series of reference marks include repeated copies of the oligo index data set, the combination of translations used to encode the reference marks may be used to assist with iterative decoding of the reference marks. For example, acceptance criteria for successful decoding of the oligo index from the reference marks may depend on reconstruction and comparison of the different copies of the oligo index data. Following each iteration Viterbi algorithm 360, shifts between pages may be corrected and the resulting copies of the oligo index data (based on their relative translations) may be compared to determine whether a confidence threshold for the oligo index data has been met. For example, reference timing may need to be fully reestablished (through insertion/deletion correction) and correction of any mutation or erasure errors may need to be addressed through ECC or consensus among copies. A CRC check may also be used for oligo index data verification. Oligo index decoder 250 may be configured to only return oligo index data with a high-level of confidence for use in further processing of the oligo read data.

In some configurations, oligo set sorter 252 may include logic to sort a received group of oligo data sequences into sets of copies. For example, the DNA amplification process may result in multiple copies of some or all oligos and oligo set sorter 252 may sort the oligo data sequences into like sequences. Sorting may be based on tagging during the sequencing process, address data (such as address data from the oligo index), and/or statistical analysis of sequences (or samples thereof) to determine repeat copies of each oligo. Note that different copies may include different errors and, at this stage, exact matching of all bases in the sequence may not be the sorting criteria. In this regard, each input oligo may generate a set of one or more oligo copies that correspond to the original input oligo data, but may not be identical copies of that data or of one another, depending on when and how the errors were introduced (thus the need for error correction). A set of oligo copies may be processed together, particularly through the first stage of processing, to determine or generate a best copy of the oligo for ECC processing.

In some configurations, reference mark decoder 254 may include logic for comparing two or more copies of an oligo to determine insertions and deletions based on reference marks with a known frequency. For example, following synthesis and identification of multiple copies of an oligo, insertion and deletion errors would have different locations for different copies and those insertions/deletions. A set of oligo copies may result from sequencing and be identified by the oligo index or other methods. Each of those copies may generate corresponding read data. In some configurations, the read data may correspond to the sequence of base pairs in the oligo and/or within a payload portion of the oligo. Each set of oligo read data may comprise the base pair sequence made up of user data with reference marks inserted at regular intervals. In some configurations, reference marks (as originally encoded) may comprise a known sequence of base pair values (which may be based on the encoded oligo index recovered by oligo index decoder 250. Pairs of oligo copies may be processed through a correlation matrix to identify insertion and deletion errors and correct the identified errors to recover the original reference mark timing, frequency, or intervals. In some configurations, a process similar to the process used by oligo index decoder 250 may be used. For example, one oligo copy may be used to generate a convolutional matrix of base pair shifts for reference mark and data positions and another oligo copy may be filtered to reference mark positions and repeated to generate a reference matrix. Those matrices may be compared by exclusive-or to populate a correlation matrix. A similar Viterbi algorithm with a Toeplitz matrix configured to manage the probability of column shifts may then be used to find the most likely path through the correlation matrix. Because two different copies of the oligo are used, a two-page correlation matrix may not be needed for determining column shifts in reference mark decoder 254. In some configurations, insertion/deletion corrections and/or probabilities from oligo index decoder 250 operating on the reference marks for oligo index data recovery may be provided to reference mark decoder 254.

In some configurations, insertion/deletion correction 256 includes logic for selectively correcting the insertion and deletion errors in an oligo, where possible. For example, insertion/deletion correction 256 may use the output from reference mark decoder 254 to determine correctable insertion/deletion errors. For example, where an insertion or deletion error has occurred between sync marks, the position of subsequent segments may be corrected for the preceding shift in base pair positions to align the symbols in segments without insertions/deletions with their expected positions in the oligo. In some configurations, reference mark decoder 254 may enable insertion/deletion correction 256 to specifically identify likely locations of insertion and/or deletion errors at the base pair level due to the 0.5 code rate.

In some configurations, erasure identifier 258 may flag segments of base pairs in the oligo as erasures in need of ECC error correction. For example, reference mark decoder 254 and related analysis may determine one or more base pairs between sync marks to be identified as erasures for error correction and/or data consensus correction 260. In some configurations, signal quality, statistical uncertainty, and/or specific thresholds for consensus may cause erasure identifier 258 to identify one or more segments as erasures because the processing by reference mark decoder 254 and/or data consensus correction 260 is inconclusive. For example, erasure identifier 258 may be configured to output an oligo that has had as many base pairs or symbols as possible positively identified as not containing insertion or deletion errors and identify (and localize) as erasures any base pairs that cannot be determined to be free of insertion or deletion errors prior to performing ECC error correction. Most commonly, placeholders inserted for identified deletions to restore reference mark timing may be identified as erasures. Note that mutation errors in DNA storage may be equivalent to the erasure errors ECC are configured to correct and need not be identified in the preprocessing stage. In some configurations, the insertion/deletion corrected output oligo base pair sequence and related erasure tags and/or soft information from reference mark decoder 254 may be the output of the preprocessing stage of decoding system 240.

In some configurations, data consensus correction 260 may include logic for using comparison of multiple preprocessed copies that have had their reference mark timing recovered to reduce the number of erasure errors and/or resolve inconclusive reference mark corrections. For example, correlation analysis across more than two copies of an oligo may allow statistical methods and soft information values to be compared to a correction threshold for deleting inserted base pairs, inserting padding or placeholder base pairs (which may be identified as erasures by erasure identifier 258), and/or correcting mutation errors that appear in a minority of copies. The correction threshold may depend on the number of copies being cross-correlated, decoder signal-to-noise ratio (SNR), size of the insertion/deletion event, a reliability value of the statistical method, and/or the error correction capabilities of the subsequent ECC processing, including the any nested ECC. In some configurations, data consensus correction 260 may be included as part of the preprocessing stage of decoding system 240.

In some configurations, one or more iterative data decoders 262 may be configured to process the output from the preprocessing stage of decoding system 240. For example, a single "best guess" copy of each unique oligo in a set of oligos for a data unit, including erasure flags and/or soft information, may be passed from preprocessing to ECC decoding. In some configurations, reference marks, address fields, and other formatting data may be removed or ignored by decoding system 240 during ECC processing. Decoding system 240 may use one or more levels of ECC decoding based on aggregating the data from a number of oligos (unique oligos rather than copies of the same oligo). For example, decoding system 240 may use LDPC codes constructed for larger codewords than can be written to or read from a single oligo. Therefore, data across multiple oligos may be aggregated to form the desired codewords. Similarly, parity or similar redundancy data may not be retrieved from each oligo and may instead be read from only a portion of the oligos or from separate parity oligos in the oligo set for the target data unit. In some configurations, ECC decoding may then be nested for increasingly aggregated sets of oligos, where each level of the nested ECC corresponds to increasingly larger codewords comprised of more oligos. Decoding system 240 may include one or more oligo aggregators and corresponding iterative decoders. For example, single level ECC encoding may use first level oligo aggregator and first level iterative encoder for codewords of 200-400 oligos. A two-level encoding scheme would use first and second level oligo aggregators and corresponding first and second level iterative encoders, such as for 200 oligo codewords at the first level and 4000 oligo codewords at the second level.

In some configurations, iterative data decoders 262 may help to ensure that the states at the codeword satisfy the parity constraint by conducting parity error checking to determine whether data has been erased or otherwise lost during data read/write processes. It may check the parity bits appended by data encoder 224 during the data encoding process, and compare them with the base pairs or symbols in the oligo sequences aggregated by the corresponding oligo aggregators. Based on the configuration of data encoder 224 in the data encoding process, each string of recovered bits may be checked to see if the "1"s total to an even or odd number for the even parity or odd parity, respectively. A parity-based post processor may also be employed to correct a specified number of the most likely error events at the output of the Viterbi-like detectors by exploiting the parity information in the coming sequence. In some configurations, iterative data decoder 262 may use soft information received from preprocessing to assist in decode decision-making. When decode decision parameters are met, the codeword may be decoded into a set of decoded base pair and/or symbol values for output or further processing by symbol decoder 264, RLL decoder 266, Cyclic Redundancy Check (CRC) 268, and/or other data postprocessing.

In some configurations, symbol decoder 264 may be configured to convert the DNA base symbols used to encode the bit data back to their bit data representations. For example, symbol decoder 264 may reverse the symbols generated by symbol encoder 222. In some configurations, symbol decoder 264 may receive the error corrected sequences from iterative decoders 262 and output a digital bit stream or bit data representation. For example, symbol decoder may receive a corrected DNA sequence listing for one or more codewords corresponding to the originally stored data unit and process the corrected DNA sequence listing through the symbol-to-bit conversion to generate a bit data sequence.

In some configurations, RLL decoder 266 may decode the run length limited codes encoded by RLL encoder 220 during the data encoding process. In some configurations, the data may go through additional post-processing or formatting to place the digital data in a conventional binary data format. For example, CRC 268 may provide a simple and reliable way to check if the decoded codeword is correct or it is a near codeword. CRC 268 may be implemented as a division of the codeword on a primitive polynomial in some Galois field. The CRC value may be determined for each binary data unit and added by the originating system or encoding system 210. For example, the remainder of the division may be stored in the codeword information for the later CRC check after decoding. CRC 268 may be particularly advantageous for DNA storage, where error rate is high and near codeword detection is more probable. After a successful CRC check, the output data 270 may then be output to a conventional binary data storage medium, network, or device, such as a host computer, network node, etc. for storage, display, and/or use as a convention binary data file or other data unit.

Figure 4C:
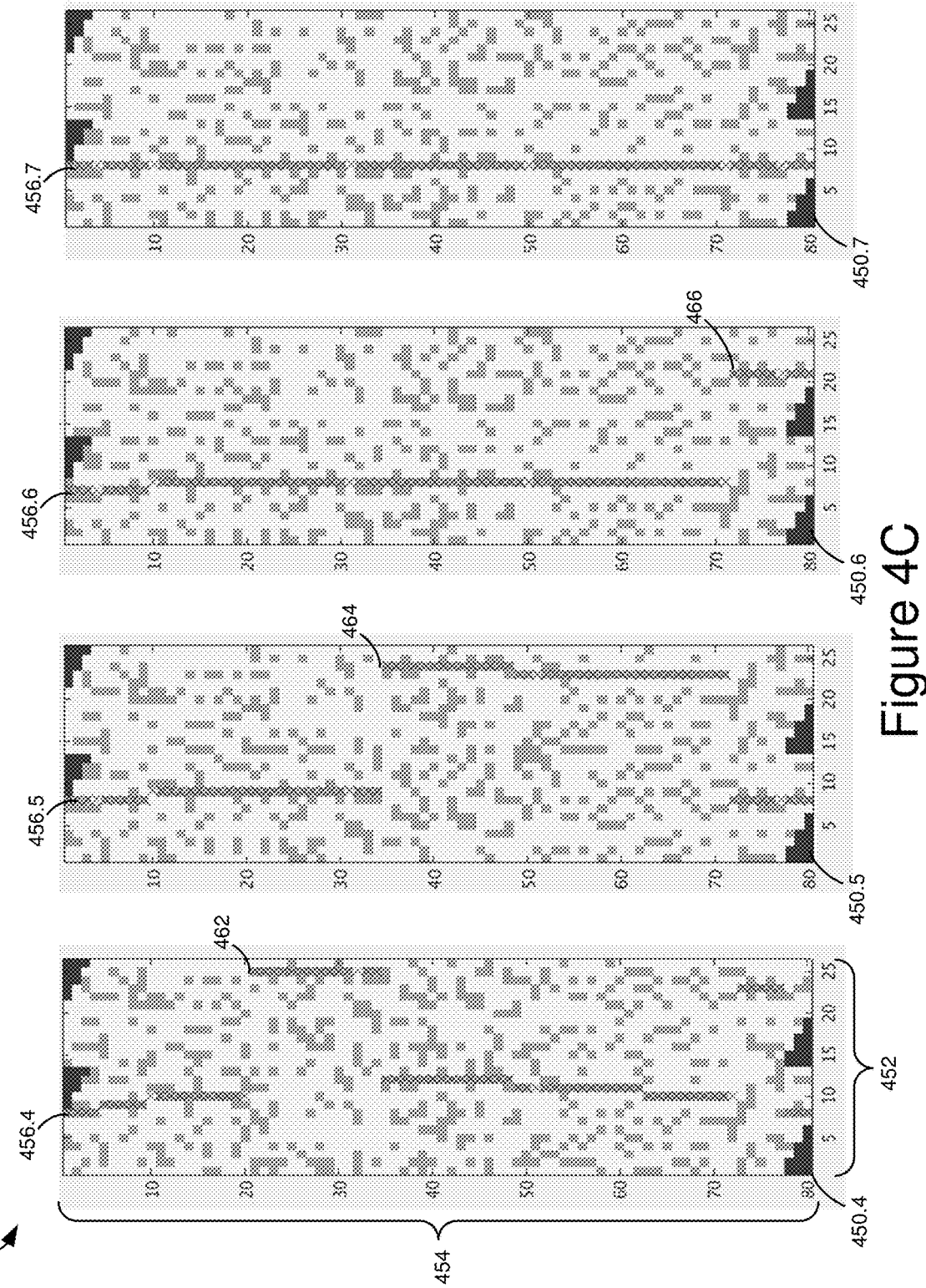
FIG. 4A is a block diagram of an oligo data processing system using embedded reference marks to restore reference mark timing and recover the oligo index.
FIG. 4B includes example correlation matrix diagrams showing different symmetries and FIG. 4C includes example correlation matrix diagrams showing iterative determination of insertion/deletion corrections to restore reference mark timing.

FIG. 4A includes an oligo data processing system 400 using embedded reference marks to determine data offsets from insertions and deletions and recover the oligo index encoded in the reference marks. In some configurations, blocks 410-442 may include logic and memory configured to execute the functions of oligo index decoder 250 in FIG. 2 and associated operations described with regard to FIGS. 3B and 3C. Blocks 410-442 may be embodied in hardware circuits and/or software modules executed using a processor and memory, such as processor 242 and memory 244 in FIG. 2. FIG. 4B includes a series of correlation matrices 402 using different oligo index copy symmetries in the reference mark processing. FIG. 4C includes a series of correlation matrices 404 as an example sequence of iterative changes to recover reference mark timing and the oligo index.

At block 410, read data for an oligo copy may be received in memory. Convolutional matrix logic 412 may generate a convolutional matrix based on separating reference mark positions and user data positions into alternating columns and then offsetting those pairs of columns by one base pair for a sequence of offset positions in both directions. Reference mark filter 414 may filter the read data based on the reference mark frequency and nominal positions of the reference marks in the encoded data, such as selecting the even base pairs in the read data sequence. User data filter 416 may filter the read data based on the reference mark frequency to select the alternating subset of base pairs corresponding to the user data positions in the encoded format. Reference matrix logic 418 may repeat the reference mark position subset for each column of one reference matrix and repeat the user data position subset for each column of another reference matrix. XOR comparator 420 may include logic to execute a XOR comparison of each corresponding value in the convolutional matrix and the two reference matrices to populate a two-page correlation matrix 422. For example, XOR comparator 420 may execute XOR logic between the values from each row of the matrices and return a 0 value for matched base pairs and a 1 value for different base pairs. The correlation matrix may be compared to the first reference matrix to generate one page of the correlation matrix and the correlation matrix may be compared to the second reference matrix to generate the second page of the correlation matrix, where the first page correlates to the reference mark positions and the second page correlates to the user data positions. Example correlation matrices 450.1-450.3 are shown in FIG. 4B, where the light gray areas indicate different base pairs and the medium gray areas indicate matched base pairs. Columns 452 correspond to shifts in reference mark position and rows 454 correspond to reference mark positions in the oligo. At this stage, the x-indicators 456 for the most likely path may not yet be determined.

Viterbi logic 430 may operate on correlation matrix 422 to determine probability values for each correlation value in the matrix based on traversing the matrix with a Viterbi algorithm. As described above, Viterbi logic 430 may be configured with a Toeplitz matrix 432 to bias the probabilities for single offset changes from the offset position of the prior reference mark position, as represented by jumps between the two pages. Viterbi logic 430 may determine a highest probability among the values in each row of correlation matrix 422, as indicated by x-indicators 456 in example correlation matrices 450. In some configurations, Viterbi logic 430 may execute for multiple traverses of correlation matrix 422 based on different symmetries in the copies of the oligo index encoded in the reference marks. Symmetry/translation selector 434 may include logic for selecting among different mirror and/or translation symmetry configurations for processing the reference marks and matrix update logic 436 may apply the selected symmetry and/or mirror configuration to reprocessing correlation matrix 422 (based on blocks 412-420) for a next iteration with Viterbi logic 430. As shown in FIG. 4B, different symmetries may be evaluated to determine the most likely path through correlation matrix 422. For example, example correlation matrix 450.1 may correspond to mirror symmetry, where oligo index copies in a 1, 2, 3, 4 order are reversed to 4, 3, 2, 1 order. Example correlation matrix 450.2 may correspond to translational symmetry, where oligo index copies in a 1, 2, 3, 4 order are translated two positions with circular translation to 3, 4, 1, 2 order. Example correlation matrix 450.3 may correspond to a combination of two position translation and mirroring, where oligo copies in a 1, 2, 3, 4 order are translated as in correlation matrix 450.2, then mirrored similarly to correlation matrix 450.1, to 2, 1, 4, 3 order. In some configurations, Viterbi logic 430 may be executed through multiple traversals, such as a first (alpha) direction traversal and a second (beta) direction traversal. The resulting probability values for each matrix position may then be summed or otherwise combined by traversal summation 438.

Most likely path logic 440 may use the probability values determined by Viterbi logic 430 directly or through the summation of multiple traversals of correlation matrix 422 to determine the most likely value (and corresponding offset column) for each row in correlation matrix 422. For example, the highest value in each row of example correlation matrices 450 may be annotated with indicator (x) 456 for the highest values, as determined by most likely path logic 440. The results of most likely path logic 440 may be evaluated by oligo index acceptance logic 442 to determine whether the reference mark alignment and copies of oligo index data along the most likely path provide sufficient confidence that the oligo index can be accurately recovered. If that threshold is not met, error correction logic 444 may use the page changes or column shifts from the prior most likely path to execute insertion and/or deletion corrections to attempt to restore the original reference mark timing. Another iteration through the Viterbi logic 430 may be initiated through matrix update logic 436, which may update correlation matrix 422 based on insertion/deletion corrections, and/or selection of alternate symmetries by selector 434.

As shown in FIG. 4C, a series of correction attempts may restore the reference timing in the reference mark positions of the data to enable recovery of the oligo index data. Correlation matrices 450.4-450.7 each include the same x-axis 452 corresponding to column shifts across the two pages and y-axis 454 corresponding to the reference mark positions. After a first iteration through correlation matrix generation and Viterbi logic 430, most likely path logic 440 determines the x-indicators 456.4 in correlation matrix 450.4. From that most likely path, error correction logic 444 may determine a deletion 462 at a page shift at reference mark position 21, insert an empty or placeholder base pair in the sequence and initiate matrix update logic 436 to rerun correlation matrix generation and most likely path determination. After the second iteration, most likely path logic 440 determines the x-indicators 456.5 in correlation matrix 450.5. From that most likely path, error correction logic 444 may determine an insertion 464 at another page shift at reference mark position 45, delete the extra base pair, and initiate matrix update logic 636 to rerun correlation matrix generation and most likely path determination. After the third iteration, most likely path logic 440 determined the x-indicators 456.6 in correlation matrix 450.6. From the most likely path, error correction logic 444 may determine another insertion 466 at another page shift at reference mark position 73, delete the extra base pair, and initiate matrix update logic 636 to rerun correlation matrix generation and most likely path determination. After the fourth iteration, most likely path logic 440 determined the x-indicators 456.7 in correlation matrix 450.7. This most likely path appears to have reference timing restored, without additional insertion or deletion errors. This reference mark pattern would meet the acceptance threshold of oligo acceptance logic 442, stop the iterations, and user the corrected reference marks to decode the oligo index data.

As shown in FIG. 5, the decoder in decoding system 240 may be operated according to an example method of recovering oligo index data stored in embedded reference marks in oligo read data, i.e., according to the method 500 illustrated by blocks 510-532.

At block 510, read data may be received for an oligo. For example, the decoder may receive a two sequence of base pairs corresponding to an oligo to be decoded.

At block 512, a convolutional matrix may be determined. For example, the decoder may separate the reference data positions from the user data positions, organize them into paired columns, and then repeat those columns for a desired number of offsets in each direction, such as 5-6 single base pair offsets.

At block 514, an oligo index copy translation pattern may be selected. For example, the decoder may be configured for the reference marks to encode multiple copies of oligo index data and may select a translation pattern that corresponds to an expected set of mirroring and circular translations that order the copies in the reference marks.

At block 516, the read data may be filtered based on the reference frequency or intervals and expected positions of the reference marks. For example, the decoder may select the even base pairs corresponding to the reference mark positions (based on a code rate of 0.5 or one base pair user data intervals) from the read data.

At block 518, a first reference matrix may be determined. For example, the decoder may repeat the base pairs from the filtered reference mark positions for each column of the reference matrix to match the number of columns in the convolutional matrix.

At block 520, the read data may be filtered based on the reference frequency or intervals and expected positions of the user data. For example, the decoder may select the odd base pairs corresponding to the user data positions (based on a code rate of 0.5 or one base pair user data intervals) from the read data.

At block 522, a second reference matrix may be determined. For example, the decoder may repeat the base pairs from the filtered user data positions for each column of the reference matrix to match the number of columns in the convolutional matrix.

At block 524, the convolutional matrix may be compared to the reference matrix. For example, the decoder may use an exclusive-or to compare the base pair values in the convolution matrix with the corresponding matrix position in each of the reference matrices in sequence.

At block 526, a two-page correlation matrix may be populated. For example, the decoder may place a corresponding value from the comparisons at block 524 in the corresponding matrix position in a correlation matrix that includes two pages, a first page of the convolutional matrix comparison to the first reference matrix and a second page of the convolutional matrix comparison to the second reference matrix.

At block 528, a most likely path through the correlation matrix may be determined. For example, the decoder may apply a Viterbi algorithm to traversing the correlation matrix to determine relative probability values in each row of the correlation matrix for possible shifts in reference mark positions between the two pages.

At block 530, oligo index recovery may be evaluated. For example, the decoder may determine whether reference mark timing has been restored and the correlation among copies of the oligo index provides a desired confidence threshold for accurately decoding the oligo index. If the reference mark timing has not been recovered and further corrections and iterations may improve reference mark recovery, method 500 may proceed to block 532. If the reference timing is recovered and the confidence threshold is met, method 500 may proceed to block 534. If the confidence threshold is not met and further corrections or iterations are not improving the reference timing recovery, have produced a number of mutation/erasure errors that are beyond consensus among copies and/or ECC correction for the oligo index data, and/or have produced variations across oligo index copies sufficient to render oligo index recovery unreliable, method 500 may proceed to block 536.

At block 532, corrections may be determined for a next iteration. For example, the decoder may correct one or more insertion/deletion errors identified by page shifts in the most likely path and return operation to block 512 for a next iteration through method 500.

At block 534, the oligo index may be decoded. For example, the decoder may successfully decode the read data corresponding to a reliable copy of the oligo index data from the reference marks and return the oligo index for use by the decoder in sorting and processing the oligo for user data recovery.

At block 536, the oligo index may be determined to be unrecoverable. For example, the decoder may determine that the error level in the oligo is too high to reliably recover the oligo index and that set of read data may be discarded.

As shown in FIG. 6, the encoder in encoding system 210 may be operated according to an example method of encoding embedded reference marks that include oligo index data in oligos, i.e., according to the method 600 illustrated by blocks 610-632.

At block 610, a data unit may be determined. For example, the encoder may receive a data unit in a conventional binary data format for storage in a set of oligos.

At block 612, user data for the oligo may be determined. For example, an oligo formatter in the encoder may select a portion of user data from the data unit to be written to a target oligo.

At block 614, an oligo index may be determined for encoding the oligo. For example, the oligo formatter may determine an oligo address and/or other syntactic information to be included in the oligo to assist with recovery of the user data and mapping it into a larger user data structure or data unit (e.g., file or data object). The set of oligo index data may be encoded with a convolutional code and selected for encoding in embedded reference marks along the length of the oligo.

At block 616, user data may be modulated. For example, an RLL encoder or similar modulator may use a modulation code selected to assure that the user data does not include the selected reference mark code.

At block 618, redundancy data may be determined. For example, the user data may be encoded using an error correction code that generates corresponding redundancy data, such as parity data.

At block 620, reference mark intervals or frequency may be determined. For example, the reference mark formatter may be configured for a reference mark interval defining the number of base pairs that should appear between sequential reference marks in the oligo, which may be a single base pair for 0.5 reference mark frequency or code rate.

At block 622, a number of copies of the oligo index data for the reference marks may be determined. For example, the encoder may divide the number of reference marks along the length of the oligo by the number of base pairs in the oligo index data to determine a number of copies of the oligo index data that will be encoded in the sequence of reference mark base pairs.

At block 624, the oligo index data may be mapped to sets of reference marks along the oligo. For example, the encoder may determine the sets of reference marks that will encode each copy of the oligo index data.

At block 626, translations for different copies of the oligo index may be determined. For example, the encoder may use a combination of mirror and circular shift translations to vary the order of the base pairs in each copy of the oligo index across the sets of reference mark base pairs.

At block 628, the translations may be ordered across the reference marks. For example, the encoder may select which translations of the oligo index are placed in which sets of reference marks along the length of the oligo to determine a final sequence of base pairs for encoding the reference marks in the oligo.

At block 630, reference marks may be inserted. For example, the reference mark inserter may insert the sequence of reference marks into the user data at the reference mark intervals to define a plurality of user data segments between each pair of sequential reference marks.

At block 632, write data for the oligo may be output for oligo synthesis. For example, the encoder may generate write data consisting of the user data segments for the target oligo and the reference marks (with embedded oligo index data) and any other added formatting data.

As shown in FIG. 7, the decoder in decoding system 240 and, more specifically, the oligo index decoder 250, may be operated according to an example method of determining probabilities of reference mark shifts using a Viterbi algorithm, i.e., according to the method 700 illustrated by blocks 710-734. In some configurations, the oligo data processing system 400 of FIG. 4 may be embodied at least in part in an oligo index decoder and execute method 700. In some configurations, method 700 may operate in the context of method 500 and, more specifically, provide further detail of the operations for block 528 on a correlation matrix populated by that method.

At block 710, a Toeplitz matrix may be determined. For example, the decoder may include a Toeplitz matrix configured to modify probabilities for single base pair offsets from a prior reference offset position to determine page changes.

At block 712, a direction may be selected for traverse. For example, the decoder may be configured to traverse the correlation matrix in a first or alpha direction, such as from the top row or start of the read data sequence to the bottom row or end of the read data sequence.

At block 714, the Viterbi algorithm may be applied to determine probabilities for each position in the matrix based on the direction of traversal. For example, the decoder may calculate probabilities for each row through the correlation matrix based on the probability values calculated for the prior row in the correlation matrix based on the direction of the traversal.

At block 716, an opposite direction may be selected for traverse. For example, the decoder may be configured to traverse the correlation matrix in a second or beta direction, such as from the bottom row or end of the read data sequence to the top row or start of the read data sequence.

At block 718, the Viterbi algorithm may be applied to determine probabilities for each position in the matrix based on the direction of traversal. For example, the decoder may make the same calculations as at block 714, but in the opposite direction.

At block 720, probabilities from the traverses may be summed. For example, the decoder may combine the results for each position in the matrix across the two traverses in opposite directions, such as by adding, averaging, or variance calculation.

At block 722, a most likely path may be selected from the sum of probabilities. For example, the decoder may evaluate the summed probabilities in each row of the matrix to determine which probability is the highest.

At block 724, whether page changes remain in the most likely path may be determined. For example, the decoder may determine that page changes between one row and the next (corresponding to adjacent positions between reference mark positions and data positions) are present in the most likely path determined at block 722. If page changes are present, method 700 may proceed to block 726. Otherwise, method 700 may proceed to block 730.

At block 726, insertions and deletions may be determined from page changes between adjacent rows. For example, the decoder may determine a next page change and whether the page change corresponds to an insertion or deletion event.

At block 728, the insertion or deletion may be corrected. For example, the decoder may use the page changes to locate insertions and deletions and delete the inserted base pair or add a placeholder base pair for the deletions to iteratively correct reference timing. Method 700 may return to block 712 for a next iteration based on the most recent correction to the reference mark timing. As described with regard to method 500, an updated correlation matrix may be populated to support the next iteration.

At block 730, the oligo index may be determined from the reference marks. For example, the decoder may use the corrected reference marks and corresponding copies of the oligo index data to determine and decode the oligo index data.

At block 732, a CRC check may be executed on the oligo index data. For example, the oligo index data may be encoded with a CRC and the encoder may perform a CRC check to confirm that the recovered oligo index data is accurate.

At block 734, the oligo index may be returned. For example, the encoder may return the decoded oligo index data for use in further decoding, recovery, and reassembly of user data into the original data unit that was stored across one or more oligos.

As shown in FIG. 8, the decoder in decoding system 240 may be operated according to an example method of correcting insertions and deletions based on embedded reference marks, i.e., according to the method 800 illustrated by blocks 810-832. In some configurations, method 800 may be executed following recovery of the oligo index data using methods 500 and/or 700. Method 800 may operate on multiple copies of the oligo that have been determined to have the same oligo index.

At block 810, the oligo index data may be used as the reference mark code for recovering the reference mark timing. For example, the decoder may receive oligo index data from an oligo index decoder that identified at least two copies of the oligo read data with the same oligo index.

At block 812, a convolutional matrix may be determined. For example, the decoder may separate the reference data positions from the user data positions from one of the oligo copies, organize them into paired columns, and then repeat those columns for a desired number of offsets in each direction, such as five single base pair offsets.

At block 814, the reference data may be determined from corrected reference marks. For example, the decoder may use corrected reference mark data from method 500 (used to determine the oligo index) as reference data for correcting reference timing for the user data.

At block 816, a reference matrix may be determined. For example, the decoder may repeat the base pairs from the corrected reference mark data for each column of the reference matrix to match the number of columns in the convolutional matrix.

At block 818, the convolutional matrix may be compared to the reference matrix. For example, the decoder may use an exclusive or to compare the base pair values in one matrix with the corresponding matrix position in the other matrix.

At block 820, a correlation matrix may be populated. For example, the decoder may place a corresponding value from the comparison at block 518 in the corresponding matrix position in a correlation matrix of the same size as the convolutional matrix and the reference matrix.

At block 822, a most likely path through the correlation matrix may be determined. For example, the decoder may apply a Viterbi algorithm to traversing the correlation matrix to determine relative probability values in each row of the correlation matrix for possible shifts in reference mark positions.

At block 824, reference mark offsets may be determined from the most likely path. For example, the decoder may interpret (relative to the most likely value in the prior row) shifts to the column on the left as one direction of offset and shifts to the column on the right as an opposite direction of offset.

At block 826, insertion and deletion errors may be determined from the offsets. For example, the decoder may evaluate the directions of the offsets as corresponding to sites of insertions or deletions in the oligo copy, such as left offsets corresponding to deletions and right offsets corresponding to insertions.

At block 828, insertion and deletion errors may be corrected in one or more of the oligo copies. For example, the decoder may include logic to insert placeholder values (which may be marked as erasures) for identified deletions at block 832 and delete base pairs identified as insertions at block 830 to compensate for errors and restore the reference mark timing of the user data segments between sequential reference marks.

Technology for improved encoding and decoding of data for DNA storage is described above. In the above description, for purposes of explanation, numerous specific details were set forth. It will be apparent, however, that the disclosed technologies can be practiced without any given subset of these specific details. In other instances, structures and devices are shown in block diagram form. For example, the disclosed technologies are described in some implementations above with reference to particular hardware.

Reference in the specification to "one embodiment" or "an embodiment" means that a particular feature, structure, or characteristic described in connection with the embodiment is included in at least one embodiment or implementation of the disclosed technologies. The appearances of the phrase "in one embodiment" in various places in the specification are not necessarily all referring to the same embodiment or implementation.

Some portions of the detailed descriptions above may be presented in terms of processes and symbolic representations of operations on data bits within a computer memory. A process can generally be considered a self-consistent sequence of operations leading to a result. The operations may involve physical manipulations of physical quantities. These quantities take the form of electrical or magnetic signals capable of being stored, transferred, combined, compared, and otherwise manipulated. These signals may be referred to as being in the form of bits, values, elements, symbols, characters, terms, numbers, or the like.

These and similar terms can be associated with the appropriate physical quantities and can be considered labels applied to these quantities. Unless specifically stated otherwise as apparent from the prior discussion, it is appreciated that throughout the description, discussions utilizing terms for example "processing" or "computing" or "calculating" or "determining" or "displaying" or the like, may refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The disclosed technologies may also relate to an apparatus for performing the operations herein. This apparatus may be specially constructed for the required purposes, or it may include a general-purpose computer selectively activated or reconfigured by a computer program stored in the computer.

Such a computer program may be stored in a computer readable storage medium, for example, but is not limited to, any type of disk including floppy disks, optical disks, CD-ROMs, and magnetic disks, read-only memories (ROMs), random access memories (RAMs), erasable programmable read-only memories (EPROMs), electrically erasable programmable read-only memories (EEPROMs), magnetic or optical cards, flash memories including USB keys with non-volatile memory or any type of media suitable for storing electronic instructions, each coupled to a computer system bus.

The disclosed technologies can take the form of an entire hardware implementation, an entire software implementation or an implementation containing both hardware and software elements. In some implementations, the technology is implemented in software, which includes but is not limited to firmware, resident software, microcode, etc.

Furthermore, the disclosed technologies can take the form of a computer program product accessible from a non-transitory computer-usable or computer-readable medium providing program code for use by or in connection with a computer or any instruction execution system. For the purposes of this description, a computer-usable or computer-readable medium can be any apparatus that can contain, store, communicate, propagate, or transport the program for use by or in connection with the instruction execution system, apparatus, or device.

A computing system or data processing system suitable for storing and/or executing program code will include at least one processor (e.g., a hardware processor) coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modems, and Ethernet cards are just a few of the currently available types of network adapters.

The terms storage media, storage device, and data blocks are used interchangeably throughout the present disclosure to refer to the physical media upon which the data is stored.

Finally, the processes and displays presented herein may not be inherently related to any particular computer or other apparatus. Various general-purpose systems may be used with programs in accordance with the teachings herein, or it may prove convenient to construct more specialized apparatus to perform the required method operations. The required structure for a variety of these systems will appear from the description above. In addition, the disclosed technologies were not described with reference to any particular programming language. It will be appreciated that a variety of programming languages may be used to implement the teachings of the technologies as described herein.

The foregoing description of the implementations of the present techniques and technologies has been presented for the purposes of illustration and description. It is not intended to be exhaustive or to limit the present techniques and technologies to the precise form disclosed. Many modifications and variations are possible in light of the above teaching. It is intended that the scope of the present techniques and technologies be limited not by this detailed description. The present techniques and technologies may be implemented in other specific forms without departing from the spirit or essential characteristics thereof. Likewise, the particular naming and division of the modules, routines, features, attributes, methodologies and other aspects are not mandatory or significant, and the mechanisms that implement the present techniques and technologies or its features may have different names, divisions and/or formats. Furthermore, the modules, routines, features, attributes, methodologies and other aspects of the present technology can be implemented as software, hardware, firmware or any combination of the three. Also, wherever a component, an example of which is a module, is implemented as software, the component can be implemented as a standalone program, as part of a larger program, as a plurality of separate programs, as a statically or dynamically linked library, as a kernel loadable module, as a device driver, and/or in every and any other way known now or in the future in computer programming. Additionally, the present techniques and technologies are in no way limited to implementation in any specific programming language, or for any specific operating system or environment. Accordingly, the disclosure of the present techniques and technologies is intended to be illustrative, but not limiting.

The invention claimed is:

1. A system, comprising:
an encoder configured to:
determine an oligo for encoding a data unit, wherein the oligo encodes a number of symbols corresponding to user data in the data unit;
insert a plurality of reference marks at a predetermined interval along a length of the oligo, wherein:
at least one set of reference marks in the plurality of reference marks encodes an oligo index; and
the predetermined interval equals a fixed data length between sequential reference marks; and
output write data for the oligo for synthesis of the oligo.

2. The system of claim 1, wherein the predetermined interval of the plurality of reference marks corresponds to a single base pair between sequential reference marks.

3. The system of claim 1, wherein the oligo index comprises:
an oligo address; and
a cyclic redundancy check code.

4. The system of claim 1, wherein the plurality of reference marks comprises a plurality of copies of the oligo index.

5. The system of claim 4, wherein:
each copy of the oligo index comprises a different set of reference marks of the at least one set of reference marks; and
at least two copies of the oligo index comprise different translations of the oligo index that order the corresponding sets of reference marks in different translation orders.

6. The system of claim 5, wherein:
each copy of the oligo index:
occupies a predetermined set of positions in the plurality of reference marks; and
has a known translation order for that predetermined set of positions and corresponding set of reference marks; and
the different translation orders are selected from:
mirror symmetry; and translational symmetry using circular offset values less than a length of the oligo index.

7. The system of claim 6, wherein:
the plurality of reference marks comprises a reference number of base pairs in the oligo;
the reference number of base pairs is a multiple of the length of the oligo index;
the multiple is at least equal to a number of the plurality of copies; and
the number of the plurality of copies is at least four.

8. The system of claim 5, wherein the different sets of reference marks of the at least two copies are interleaved along the length of the oligo index.

9. A system comprising:
an index decoder configured to:
receive read data determined from sequencing an oligo, wherein:
the oligo encodes:
a number of symbols corresponding to user data in a data unit; and
a plurality of reference marks at a predetermined interval along a length of the oligo;
at least one set of reference marks in the plurality of reference marks encodes an oligo index; and
the predetermined interval equals a fixed data length between sequential reference marks;
determine, from the read data, a convolutional matrix for the oligo, wherein each column of the convolutional matrix corresponds to a base pair offset of the read data for the oligo;
determine, from the read data, a first reference matrix based on a first sequence of reference positions at an encoded frequency of the plurality of reference marks;
determine, from the read data, a second reference matrix based on a second sequence of reference positions at the encoded frequency of the plurality of reference marks;
determine a first correlation matrix based on a comparison of the convolutional matrix to the first reference matrix;
determine a second correlation matrix based on a comparison of the convolutional matrix and the second reference matrix;
determine a most likely path through a combination of the first correlation matrix and the second correlation matrix based on:
a series of probabilities of moving between corresponding rows in the first correlation matrix and the second correlation matrix; and
loop decoding for different symmetries of a plurality of copies of the oligo index; and
decode the oligo index based on the most likely path and the plurality of copies of the oligo index.

10. The system of claim 9, further comprising:
a reference mark decoder configured to:
receive, based on oligos with a same decoded oligo index, read data determined from sequencing at least two copies of the oligo;
populate a reference mark correlation matrix based on a comparison of reference mark positions in a first copy of the oligo to reference mark positions in a second copy of the oligo;
determine a most likely path through the reference mark correlation matrix corresponding to offset values for the plurality of reference marks;

determine, based on at least one offset value for the plurality of reference marks, an insertion or deletion in a data segment between sequential reference marks; and correct symbol alignment in the data segment to compensate for the insertion or deletion; and a user data decoder configured to:

decode the user data from the read data using an error correction code and corresponding redundancy data; and output, based on the decoded user data, the data unit.

11. A method comprising:

determining an oligo for encoding a data unit, wherein the oligo encodes a number of symbols corresponding to user data in the data unit;

inserting a plurality of reference marks at a predetermined interval along a length of the oligo, wherein:

at least one set of reference marks in the plurality of reference marks encodes an oligo index; and the predetermined interval equals a fixed data length between sequential reference marks; and outputting write data for the oligo for synthesis of the oligo.

12. The method of claim 11, wherein the predetermined interval of the plurality of reference marks corresponds to a single base pair between sequential reference marks.

13. The method of claim 11, wherein the oligo index comprises:

an oligo address; and a cyclic redundancy check code.

14. The method of claim 11, wherein:

the plurality of reference marks comprises a plurality of copies of the oligo index;

each copy of the oligo index comprises a different set of reference marks of the at least one set of reference marks; and at least two copies of the oligo index comprise different translations of the oligo index that order the corresponding sets of reference marks in different translation orders.

15. The method of claim 14 wherein:

each copy of the oligo index:

occupies a predetermined set of positions in the plurality of reference marks; and has a known translation order for that predetermined set of positions and corresponding set of reference marks; and the different translation orders are selected from:

mirror symmetry; and translational symmetry using circular offset values less than a length of the oligo index.

16. The method of claim 15, wherein:

the plurality of reference marks comprises a reference number of base pairs in the oligo;

the reference number of base pairs is a multiple of the length of the oligo index;

the multiple is at least equal to a number of the plurality of copies; and the number of the plurality of copies is at least four.

17. The method of claim 14, wherein the different sets of reference marks of the at least two copies are interleaved along the length of the oligo index.

18. The method of claim 14, further comprising:

receiving read data determined from sequencing the oligo;

determining, from the read data, a convolutional matrix for the oligo, wherein each column of the convolutional matrix corresponds to a base pair offset of the read data for the oligo;

determining, from the read data, a first reference matrix based on a first sequence of reference positions at an encoded frequency of the plurality of reference marks;

determining, from the read data, a second reference matrix based on a second sequence of reference positions at the encoded frequency of the plurality of reference marks;

determining a first correlation matrix based on a comparison of the convolutional matrix to the first reference matrix;

determining a second correlation matrix based on a comparison of the convolutional matrix and the second reference matrix;

determining a most likely path through a combination of the first correlation matrix and the second correlation matrix based on:

a series of probabilities of moving between corresponding rows in the first correlation matrix and the second correlation matrix; and loop decoding for different symmetries of the plurality of copies of the oligo index; and decoding the oligo index based on the most likely path and the plurality of copies of the oligo index.

19. The method of claim 18, further comprising:

receiving, based on oligos with a same decoded oligo index, read data determined from sequencing at least two copies of the oligo;

populating a reference mark correlation matrix based on a comparison of reference mark positions in a first copy of the oligo to reference mark positions in a second copy of the oligo;

determining a most likely path through the reference mark correlation matrix corresponding to offset values for the plurality of reference marks;

determining, based on at least one offset value for the plurality of reference marks, an insertion or deletion in a data segment between sequential reference marks;

correcting symbol alignment in the data segment to compensate for the insertion or deletion;

decoding the user data from the read data using an error correction code and corresponding redundancy data; and outputting, based on the decoded user data, the data unit.

20. A system comprising:

means for determining an oligo for encoding a data unit, wherein the oligo encodes a number of symbols corresponding to user data in the data unit;

means for inserting a plurality of reference marks at a predetermined interval along a length of the oligo, wherein:

at least one set of reference marks in the plurality of reference marks encodes an oligo index; and the predetermined interval equals a fixed data length between sequential reference marks; and means for outputting write data for the oligo for synthesis of the oligo.

* * * * *